US009695393B2

(12) United States Patent
Nankervis et al.

(10) Patent No.: US 9,695,393 B2
(45) Date of Patent: Jul. 4, 2017

(54) CONCENTRATING COMPONENTS OF FLUID CIRCULATED THROUGH A CELL GROWTH CHAMBER

(71) Applicant: Terumo BCT, Inc., Lakewood, CO (US)

(72) Inventors: Brian J. Nankervis, Thornton, CO (US); Thomas G. DiLorenzo, Arvada, CO (US); Michael E. Kinzie, Lafayette, CO (US); Mark E. Jones, Littleton, CO (US)

(73) Assignee: Terumo BCT, Inc., Lakewood, CO (US)

( * ) Notice: Subject to any disclaimer, the term of this patent is extended or adjusted under 35 U.S.C. 154(b) by 357 days.

(21) Appl. No.: 13/971,652

(22) Filed: Aug. 20, 2013

(65) Prior Publication Data

US 2014/0051167 A1 Feb. 20, 2014

Related U.S. Application Data

(60) Provisional application No. 61/691,246, filed on Aug. 20, 2012.

(51) Int. Cl.
*C12N 5/00* (2006.01)
*C12M 1/00* (2006.01)
*B01D 61/14* (2006.01)
*C12M 1/12* (2006.01)
*B01D 61/22* (2006.01)
*B01D 63/02* (2006.01)

(52) U.S. Cl.
CPC ............ *C12M 47/02* (2013.01); *B01D 61/14* (2013.01); *B01D 61/22* (2013.01); *B01D 63/02* (2013.01); *C12M 25/12* (2013.01); *C12M 29/16* (2013.01); *B01D 2311/12* (2013.01)

(58) Field of Classification Search
CPC .................................. C12N 5/00; C12N 5/06
See application file for complete search history.

(56) References Cited

U.S. PATENT DOCUMENTS 5,162,225 A 11/1992 Sager et al.
6,001,585 A * 12/1999 Gramer .................. C12M 23/24
435/182
2006/0019391 A1 1/2006 Marx et al.
2011/0212493 A1 * 9/2011 Hirschel ................ C12M 23/28
435/91.4
2012/0086657 A1 4/2012 Stanton, IV et al.
2012/0088224 A1 4/2012 DiLorenzo et al.

FOREIGN PATENT DOCUMENTS

WO 2004/000444 A1 12/2003
WO 2008/109674 A2 9/2008
WO 2011/091248 A1 7/2011

OTHER PUBLICATIONS

International Search Report and Written Opinion, PCT/US2013/055866, Nov. 4, 2013.
First Office Action, Chinese Patent Application No. 201380043369.4, Jan. 15, 2016 (English language translation included).
Second Office Action, Chinese Patent Application No. 201380043369A, Jul. 28, 2016 (English language translation included).
Brandwein, Harvey, "Single-use Filtration Systems for Harvest and Volume Reduction of Cell-based Therapeutics", International Society for Cellular Therapy, Webinar, Feb. 8, 2012.
Third Office Action, Chinese Patent Application No. 201380043369.4, Feb. 10, 2017 (English language translation included).

* cited by examiner

*Primary Examiner* — Ruth Davis
(74) *Attorney, Agent, or Firm* — René A. Pereyra; Elizabeth J. Reagan; John R. Merkling

(57) ABSTRACT

One or more embodiments are described directed to a method and system for concentrating components of a fluid circulated through a cell growth chamber such as a cell growth chamber. Accordingly, embodiments include methods and systems that utilize a tangential flow filter to concentrate components of a fluid that in embodiments includes expanded cells. In embodiments, a concentrated fluid component and a concentrated cell component are generated by flowing the fluid with expanded cells across a tangential flow filter. The concentrated cell component may be recirculated to the tangential flow filter to reach some desired concentration of cells. The concentrated fluid component may be collected to utilize cellular-produced constituents in the concentrated fluid component.

5 Claims, 11 Drawing Sheets

CONCENTRATING COMPONENTS OF FLUID CIRCULATED THROUGH A CELL GROWTH CHAMBER

CROSS-REFERENCE TO RELATED PATENT APPLICATIONS

This patent application claims priority to U.S. Provisional Patent Application No. 61/691,246 entitled "CONCENTRATING COMPONENTS OF FLUID CIRCULATED THROUGH A CELL GROWTH CHAMBER," filed on Aug. 20, 2012, and hereby incorporated by reference in its entirety as if set forth herein in full.

BACKGROUND

Cell Expansion Systems (CESs) are used to expand and differentiate cells. Cell expansion systems are known in the art. For example, U.S. Pat. Nos. 5,162,225 and 6,001,585 generally describe cell expansion systems designed for cell expansion.

The potential use of stem cells in a variety of treatments and therapies has achieved particular attention. Cell expansion systems can be used to expand, e.g., grow, stem cells, as well as other types of cells, such as bone marrow cells. Stem cells which are expanded from donor cells can be used to repair or replace damaged or defective tissues and have broad clinical applications for a wide range of diseases. Recent advances in the regenerative medicine field demonstrates that stem cells have properties such as proliferation and self-renewal capacity, maintenance of the unspecialized state, and the ability to differentiate into specialized cells under particular conditions.

Cell expansion systems include one or more compartments for expanding the cells, such as a cell growth chamber, (e.g., a bioreactor). After expansion, the cells are typically concentrated before being used.

Embodiments of the present invention have been made in light of these and other considerations. However, the relatively specific problems discussed above do not limit the applicability of the embodiments of the present invention to other problems or uses.

SUMMARY

It is to be understood that the present invention may include a variety of different versions or embodiments, and this Summary is not meant to be limiting or all-inclusive. Rather, this Summary is provided to introduce aspects of some embodiments of the present invention in a simplified form, and is not intended to identify key or essential elements of the claimed invention, nor is it intended to limit the scope of the claims. This Summary provides some general descriptions of features that may be included in embodiments, and also includes some more specific descriptions of other features that may be included in embodiments.

One or more embodiments are generally directed to a method and system for concentrating a component from a fluid circulated in a cell growth chamber. The embodiments include circulating a fluid within a cell growth chamber that contains cells. A first fluid that is circulated through the cell growth chamber is removed from the cell growth chamber. The first fluid is circulated across a tangential flow filter that is fluidly associated with the cell growth chamber to generate a concentrated fluid component. At least a portion of the concentrated fluid component is collected in a container.

Other embodiments are generally directed to a method and system for removing expanded cells from the cell growth chamber using a first fluid. The first fluid with the expanded cells is then circulated across a tangential flow filter that is fluidly associated with the cell growth chamber to generate a concentrated fluid component and a concentrated cell component. The concentrated fluid component is collected in a container. In embodiments, the concentrated cell component may also be collected in a container. In other embodiments, the concentrated cell component may be recirculated to the tangential flow filter until a predetermined concentration of cells is achieved.

As used herein, "at least one," "one or more," and "and/or" are open-ended expressions that are both conjunctive and disjunctive in operation. For example, each of the expressions "at least one of A, B and C," "at least one of A, B, or C," "one or more of A, B, and C," "one or more of A, B, or C" and "A, B, and/or C" means A alone, B alone, C alone, A and B together, A and C together, B and C together, or A, B and C together.

Additional advantages of the embodiments presented herein will become readily apparent from the following discussion, particularly when taken together with the accompanying drawings.

BRIEF DESCRIPTION OF THE DRAWINGS

To further clarify the above and other advantages and features of the present invention, a more particular description of the invention will be rendered by reference to specific embodiments thereof which are illustrated in the drawings. It is appreciated that these drawings depict only embodiments of the invention and are therefore not to be considered limiting of its scope.

DETAILED DESCRIPTION

Figure 1:
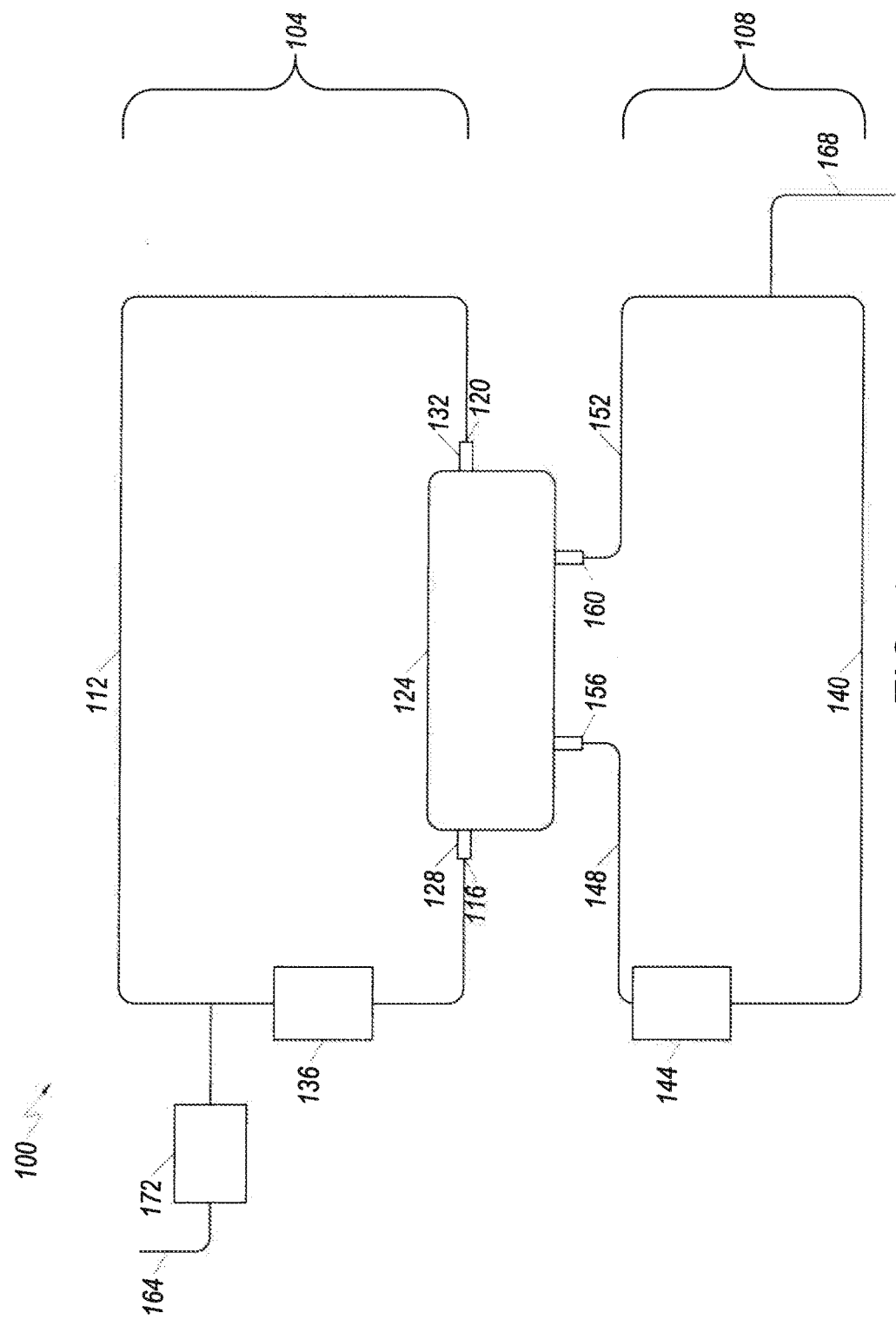
FIG. 1 depicts one embodiment of a cell expansion system (CES)

The principles of the present invention may be further understood by reference to the following detailed description and the embodiments depicted in the accompanying drawings. It should be understood that although specific features are shown and described below with respect to detailed embodiments, the present invention is not limited to the embodiments described below.

Reference will now be made in detail to the embodiments illustrated in the accompanying drawings and described below. Wherever possible, the same reference numbers are used in the drawings and the description to refer to the same or like parts.

A schematic of an embodiment of a cell expansion system (CES) 100 is depicted in FIG. 1. CES 100 includes first fluid circulation path 104 and second fluid circulation path 108. First fluid flow path 112, which is part of first fluid circulation path 104, has ends 116 and 120 fluidly associated with a growth chamber 124, such as a bioreactor. Specifically, end 116 is fluidly associated with a first inlet 128 of cell growth chamber 124, and end 120 is fluidly associated with first outlet 132 of cell growth chamber 124. In embodiments, fluid in first circulation path 104 flows through the interior of hollow fibers of a hollow fiber membrane disposed in cell growth chamber 124 (cell growth chambers and hollow fiber membranes are described in more detail infra). Further, first fluid flow controller 136 may be operably connected to first fluid flow path 112, to control the flow of fluid in first circulation path 104.

Second fluid circulation path 108 includes second fluid flow path 140, cell growth chamber 124, and a second fluid flow controller 144. The second fluid flow path 140 has at least ends 148 and 152. Ends 148 and 152 of second fluid flow path 140 are fluidly associated with inlet port 156 and outlet port 160 respectively of cell growth chamber 124. Fluid flowing through cell growth chamber 124 may be in contact with the outside of a hollow fiber membrane in the cell growth chamber 124. In some embodiments, second fluid circulation path 108 may be operably connected to second fluid flow controller 144.

Figure 10:
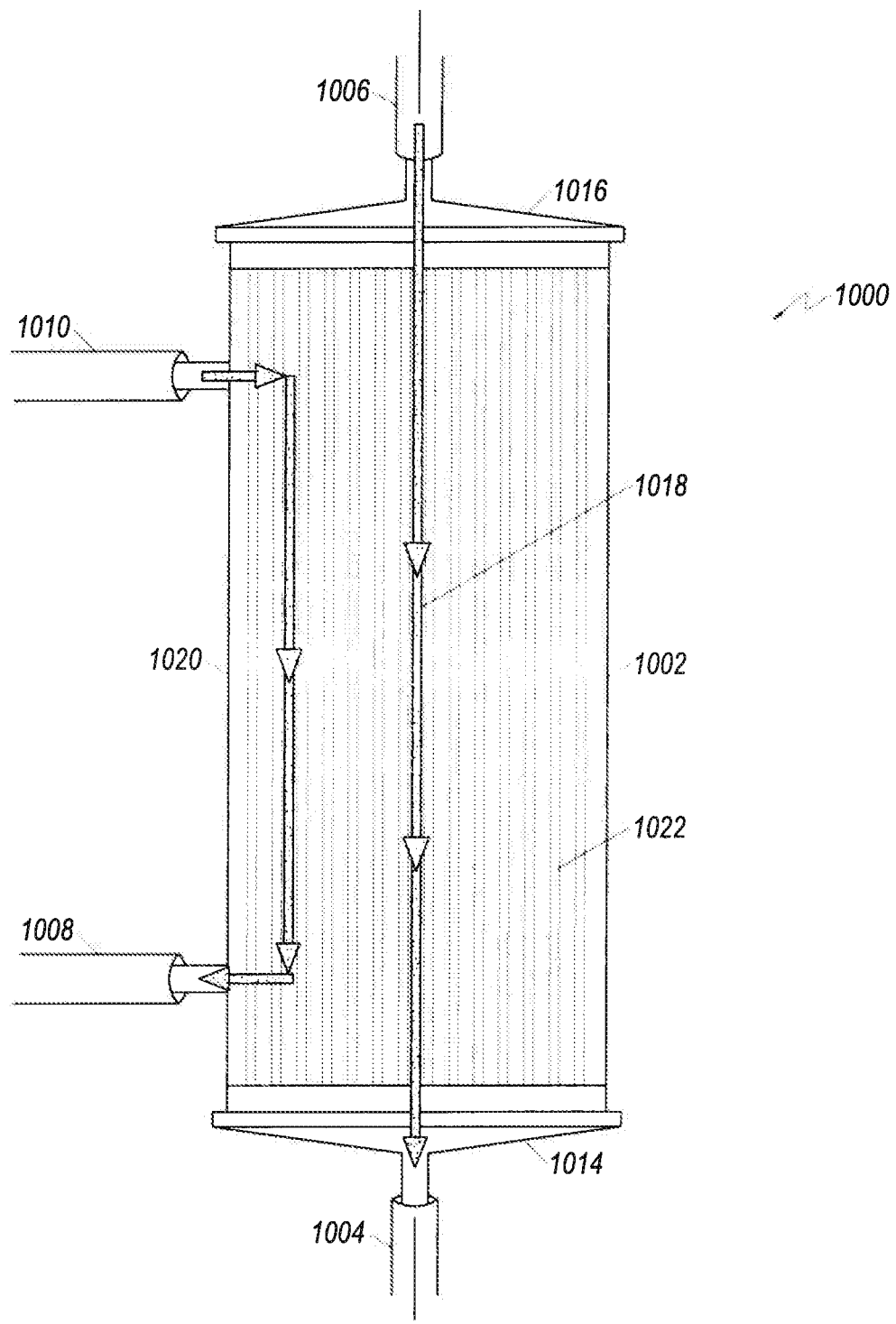
FIG. 10 illustrates a hollow fiber membrane device that may be used as a tangential flow filter and/or a cell growth chamber with embodiments of the present disclosure.

In embodiments, first and second fluid circulation paths 104 and 108 are separated in cell growth chamber 124 by a hollow fiber membrane. Thus in these embodiments, fluid in first fluid circulation path 104 flows through intracapillary ("IC") space of the hollow fibers in the cell growth chamber. First circulation path 104 may be referred to as the "IC loop." In these embodiments, fluid in second circulation path 108 flows through the extracapillary ("EC") space in the cell growth chamber. Second fluid circulation path 108 may thus be referred to as the "EC loop." Fluid in first fluid circulation path 104 can flow in either a co-current or counter-current direction with respect to flow of fluid in second fluid circulation path 108. FIG. 10 illustrates an example of a hollow fiber membrane device that may be used as cell growth chamber in some embodiments. In other embodiments, the cell growth chamber 124 is not a hollow fiber membrane device.

Fluid inlet path 164 may be fluidly associated with first fluid circulation path 104. Fluid inlet path 164 allows fluid into first fluid circulation path 104, while fluid outlet path 168 allows fluid to leave CES 100. Third fluid flow controller 172 may be operably associated with fluid inlet path 164. In other embodiments, third fluid flow controller 172 may be alternatively be associated with first outlet path 168.

Fluid flow controllers as used herein may, in embodiments, include a pump, valve, clamp, or combinations thereof. In embodiments, multiple pumps, valves, and clamps can be arranged in any combination. In various embodiments, the fluid flow controller is or includes a peristaltic pump. In embodiments, fluid circulation paths, inlet ports, and outlet ports can be constructed of tubing of any material.

Various components are referred to herein as "operably associated." As used herein, "operably associated" refers to components that are linked together in operable fashion, and encompasses embodiments in which components are linked directly, as well as embodiments in which additional components are placed between the two linked components. "Operably associated" components can be "fluidly associated." "Fluidly associated" refers to components that are linked together such that fluid can be transported between them. "Fluidly associated" encompasses embodiments in which additional components are disposed between the two fluidly associated components, as well as components that are directly connected. Fluidly associated components can include components that do not contact fluid, but contact other components to manipulate the system (e.g. a peristaltic pump that pumps fluids through flexible tubing by compressing the exterior of the tube).

Generally, any kind of fluid, including buffers, media, protein peptide containing fluid, and cell or cell component-containing fluid can flow through the various circulations paths, inlet paths, and outlet paths.

Figure 2:
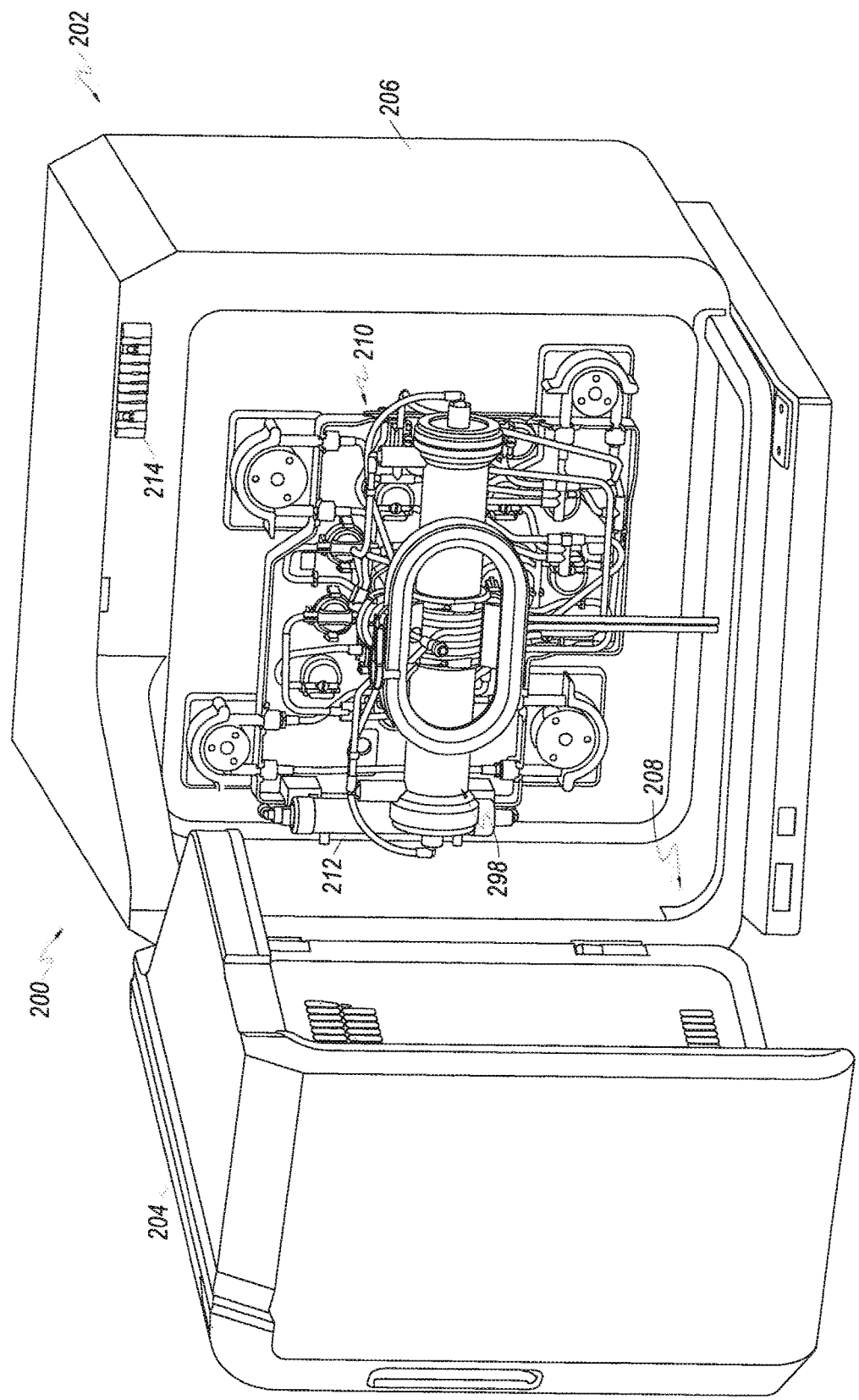
FIG. 2 illustrates a perspective view of a cell expansion system with a premounted fluid conveyance device that may be used with embodiments of the present disclosure.

Turning to FIG. 2, another embodiment of a cell expansion system 200 with a premounted fluid conveyance assembly is shown in accordance with embodiments of the present disclosure. The CES 200 includes a cell expansion machine 202 that comprises a hatch or closable door 204 for engagement with a back portion 206 of the cell expansion machine 202. An interior space 208 within the cell expansion machine 202 includes features adapted for receiving and engaging a premounted fluid conveyance assembly, shown in this embodiment as premounted fluid conveyance assembly 210. The premounted fluid conveyance assembly 210 is detachably-attachable to the cell expansion machine 202 to facilitate relatively quick exchange of a new or unused premounted fluid conveyance assembly 210 at a cell expansion machine 202 for a used premounted fluid conveyance assembly 210 at the same cell expansion machine 202. In embodiments, a single cell expansion machine 202 can be operated to grow or expand a first set of cells using a first premounted fluid conveyance assembly 210, and thereafter, used to grow or expand a second set of cells using a second premounted fluid conveyance assembly 210 without the cell expansion machine 202 needing to be sanitized between interchanging the first premounted fluid conveyance assembly 210 for a second premounted fluid conveyance assembly 210. The premounted fluid conveyance assembly 210 may include a cell growth chamber 298 and an oxygenator 212. Tubing guide slots are shown as 214 for receiving various media tubing connected to premounted fluid conveyance assembly 210.

Figure 3:
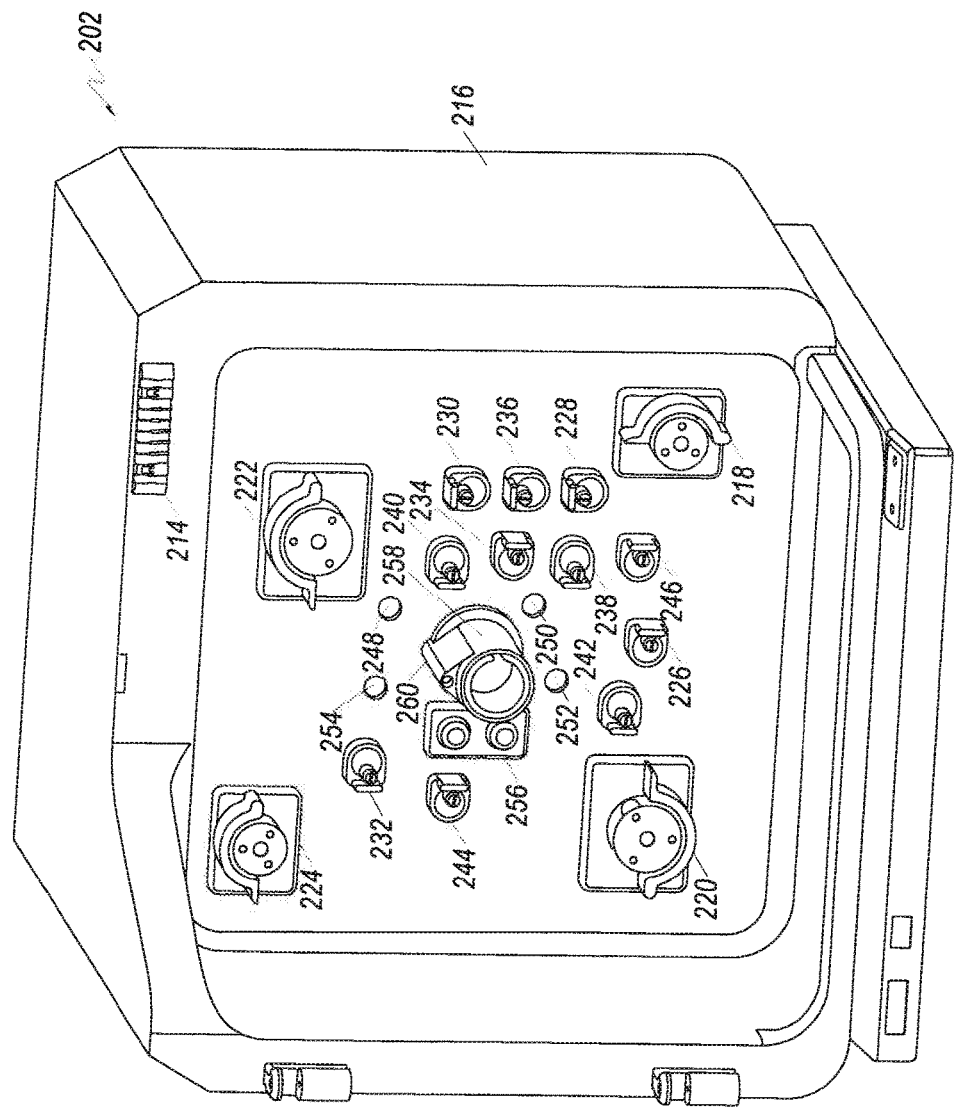
FIG. 3 depicts a perspective view of the housing of a cell expansion system that may be used with embodiments of the present disclosure.

Next, FIG. 3 illustrates the back portion 216 of cell expansion machine 202 prior to detachably-attaching a premounted fluid conveyance assembly 210 (see FIG. 2), in accordance with embodiments of the present disclosure. The closable door 204 (shown in FIG. 2) is omitted from FIG. 3. The back portion 216 of the cell expansion machine 202 includes a number of different structures for working in combination with elements of a premounted fluid conveyance assembly 210. More particularly, the back portion 216 of the cell expansion machine 202 includes a plurality of peristaltic pumps for cooperating with pump loops on the premounted fluid conveyance assembly 210, including the IC circulation pump 218, the EC circulation pump 220, the IC inlet pump 222, and the EC inlet pump 224. In addition, the back portion 216 of the cell expansion machine 202 includes a plurality of valves, including the IC circulation valve 226, the reagent valve 228, the IC media valve 230, the air removal valve 232, the cell inlet valve 234, the wash valve 236, the distribution valve 238, the EC media valve 240, the IC waste valve 242, the EC waste valve 244, and the harvest valve 246. Several sensors are also associated with the back portion 216 of the cell expansion machine 202, including the IC outlet pressure sensor 248, the combination IC inlet pressure and temperature sensors 250, the combination EC inlet pressure and temperature sensors 252, and the EC outlet pressure sensor 254. Also shown is the optical sensor 256 for the air removal chamber 212 (FIG. 2).

In accordance with embodiments, a shaft or rocker control 258 for rotating the cell growth chamber 124 is shown. Shaped fitting 260 associated with the shaft 258 allows for proper alignment of a shaft access aperture, see e.g., aperture 424 (FIG. 4) of a tubing-organizer, see e.g., tubing organizer 300 (FIG. 4) of a premounted conveyance assembly (210 or 400, see FIG. 4) with the back portion 216 of the cell expansion machine 202. Rotation of rocker control 258 imparts rotational movement to shaft fitting 260 and cell growth chamber 298. Thus, when an operator of the CES 200 attaches a new and/or sterile premounted fluid conveyance assembly to the cell expansion machine 200, the alignment is a relatively simple matter of properly orienting the shaft access aperture, e.g., aperture 424 of a premounted fluid conveyance assembly with the shaped fitting 260.

Figure 4:
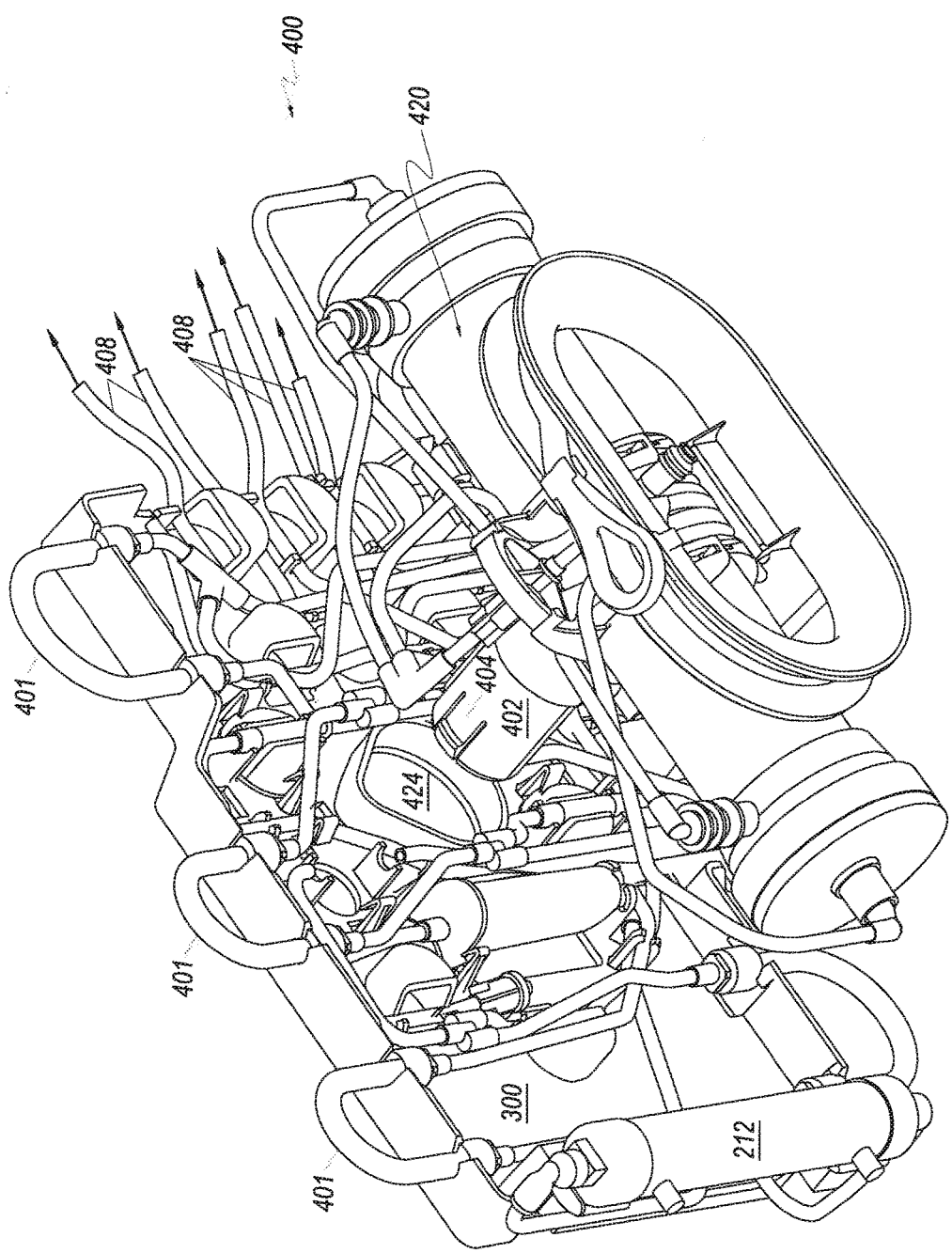
FIG. 4 illustrates a perspective view of an embodiment of a premounted fluid conveyance device that may be used with embodiments of the present disclosure.

Turning to FIG. 4, a perspective view of another embodiment of a detachably-attachable premounted fluid conveyance assembly 400 is shown. The premounted fluid conveyance assembly 400 may be detachably-attachable to the cell expansion machine 202 to facilitate relatively quick exchange of a new or unused premounted fluid conveyance assembly 400 at a cell expansion machine 202 for a used premounted fluid conveyance assembly 400 at the same cell expansion machine 202. As shown in FIG. 4, a cell growth chamber 420 is attached to a cell growth chamber coupling that includes a shaft fitting 402. The shaped fitting 402 includes one or more shaft fastening mechanisms, such as a biased arm or spring member 404 for engaging a shaft, e.g., 258 (shown in FIG. 3) of a cell expansion machine, such as cell expansion machine 202.

According to embodiments, the premounted fluid conveyance assembly 400 typically includes tubing 408 and various tubing fittings to provide the fluid paths shown in FIGS. 5-9, as discussed below. Pump loops 401 are also provided. Although the various media may be provided at the site where the cell expansion machine 202 is located, the premounted fluid conveyance assembly 400 may include sufficient tubing length to extend to the exterior of a cell expansion machine, e.g., 202, and to enable welded connections to tubing associated with containers such as, media bags.

Figure 5:
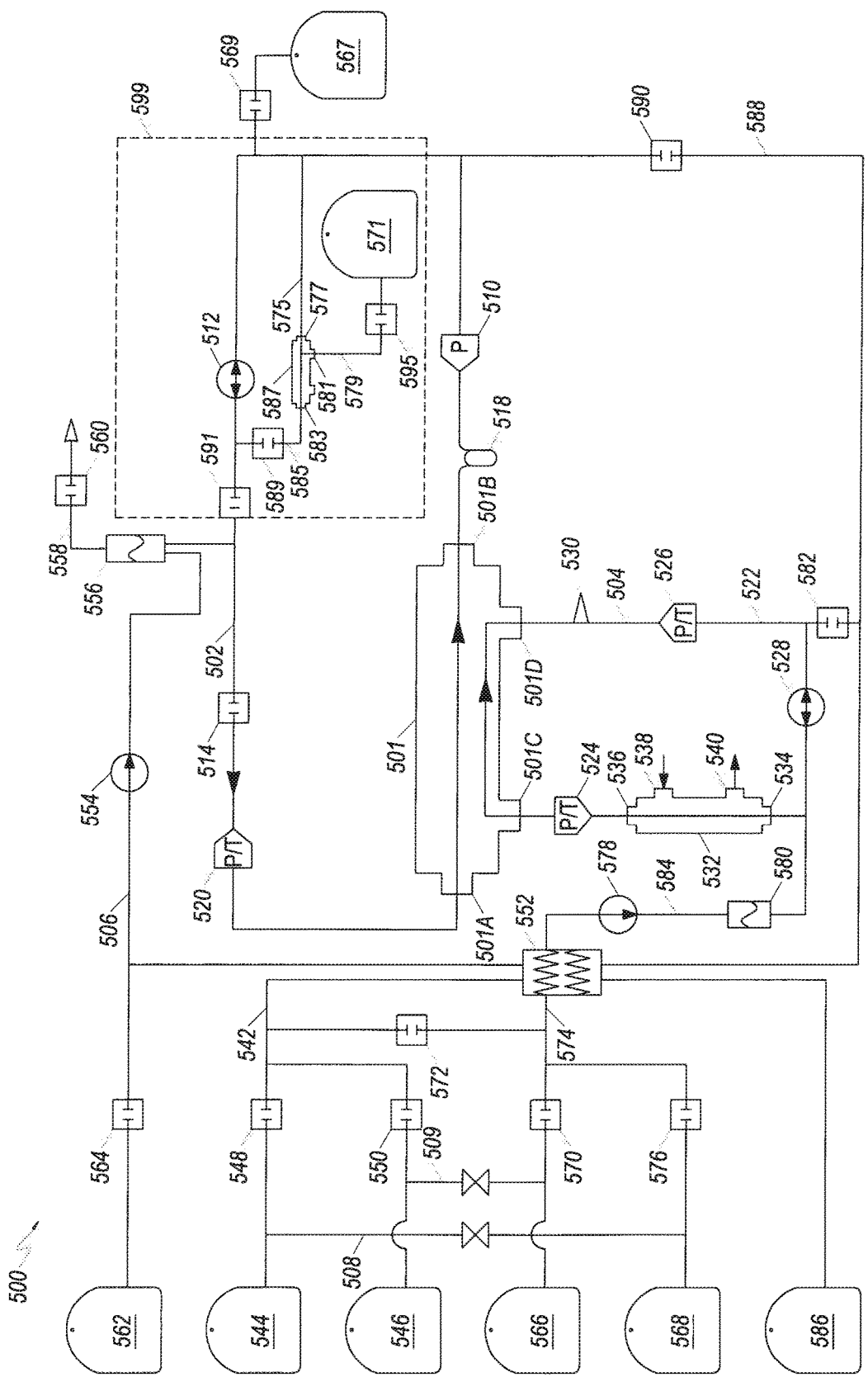
FIG. 5 depicts a schematic of a cell expansion system in accordance with an embodiment of the present disclosure.
Figure 6:
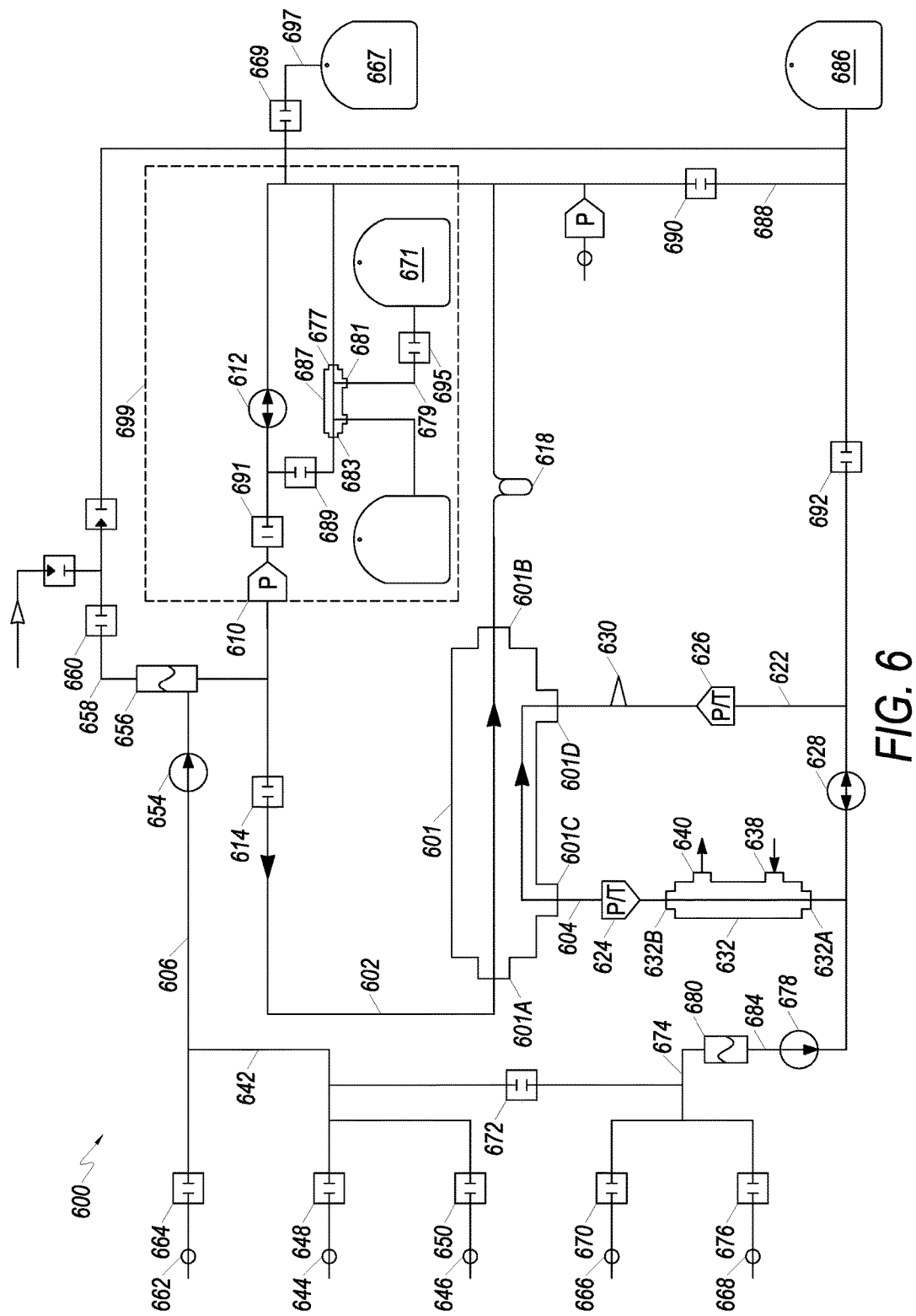
FIG. 6 illustrates a schematic of another embodiment of a cell expansion system in accordance with another embodiment of the present disclosure.

FIG. 5 illustrates a schematic of an embodiment of a cell expansion system 500, and FIG. 6 illustrates a schematic of another embodiment of a cell expansion system 600. In the embodiments shown in FIGS. 5 and 6, and described below, the cells are grown in the IC space. However, the disclosure is not limited to such examples and may in other embodiments provide for cells to be grown in the EC space.

FIG. 5 illustrates a CES 500, which includes first fluid circulation path 502 (also referred to as the "intracapillary loop" or "IC loop") and second fluid circulation path 504 (also referred to as the "extracapillary loop" or "EC loop"). In embodiments, first fluid flow path 506 is fluidly associated with cell growth chamber 501 to form first fluid circulation path 502. Fluid may flow into cell growth chamber 501 through IC inlet port 501A, and in some embodiments, through hollow fibers in cell growth chamber 501 (e.g., a bioreactor where cells are grown or expanded), and exits via IC outlet port 501B. Pressure gauge 510 measures the pressure of media leaving cell growth chamber 501. Media may flow through IC circulation pump 512 which can be used to control the rate of media flow. IC circulation pump 512 may pump the fluid in a first direction or second direction opposite the first direction. Exit port 501B can be used as an inlet in the reverse direction. Media entering the IC loop may enter through valve 514. As those skilled in the art will appreciate, additional valves and/or other devices can be placed at various locations to isolate and/or measure characteristics of the media along portions of the fluid paths. Accordingly, it is to be understood that the schematic shown represents one possible configuration for various elements of the CES 500 and modifications to the schematic shown are within the scope of the one or more present embodiments.

With regard to the IC loop, samples of media can be obtained from sample coil 518 during operation. Pressure/temperature gauge 520 disposed in first fluid circulation path 502 allows detection of media pressure and temperature during operation. Media then returns to IC inlet port 501A to complete fluid circulation path 502. Cells grown/expanded in cell growth chamber 501 may be flushed out of cell growth chamber 501 into outlet container 567 through valve 569; into outlet container 567 through valve 589, and TFF 587; or redistributed within the hollow fibers in growth chamber 501 through valve 591 for further growth. This will be described in more detail below.

Fluid in second fluid circulation path 504 may enter cell growth chamber 501 via EC inlet port 501C, and leave cell growth chamber 501 via EC outlet port 501D. Media in the EC loop is, in embodiments, in contact with the outside of the hollow fibers in the cell growth chamber 501, thereby allowing diffusion of small molecules into and out of the hollow fibers in the cell growth chamber 501.

Pressure/temperature gauge 524 disposed in the second fluid circulation path 504 allows the pressure and/or temperature of media to be measured before the media enters the EC space of the cell growth chamber 501. Pressure/temperature gauge 526 allows the pressure and/or temperature of media in the second fluid circulation path 504 to be measured after it leaves the cell growth chamber 501. With regard to the EC loop, samples of media can be obtained, in embodiments, from sample port 530 or a sample coil during operation.

After leaving EC outlet port 501D of cell growth chamber 501, fluid in second fluid circulation path 504, in embodiments, passes through EC circulation pump 528 to oxygenator 532. EC circulation pump 528 may also pump the fluid in opposing directions. Second fluid flow path 522 is fluidly associated with oxygenator 532 via oxygenator inlet port 534 and oxygenator outlet port 536. In operation, fluid media flows into oxygenator 532 via oxygenator inlet port 534, and exits oxygenator 532 via oxygenator outlet port 536. Oxygenator 532 adds oxygen to and removes bubbles from media in the CES. In various embodiments, media in second fluid circulation path 504 is in equilibrium with gas entering oxygenator 532. The oxygenator 532 can be any appropriately sized oxygenator or gas transfer device known in the art. Air or gas flows into oxygenator 532 via filter 538 and out of oxygenator or gas transfer device 532 through filter 540. Filters 538 and 540 reduce or prevent contamination of oxygenator 532 and associated media. Air or gas purged from the CES 500 during portions of a priming sequence can vent to the atmosphere via the oxygenator 532.

In embodiments, fluid media in first fluid circulation path 502 and second fluid circulation path 504 flows through cell growth chamber 501 in the same direction (a co-current configuration). The CES 500 can also be configured in other embodiments to flow in a counter-current conformation.

In accordance with at least one embodiment, media, including cells (from container 562), and fluid media from container 546 can be introduced to first fluid circulation path 502 via first fluid flow path 506. Fluid container 562 (e.g., cell inlet bag or saline priming fluid for priming air out of the system) is fluidly associated with the first fluid flow path 506 and the first fluid circulation path 502 via valve 564.

Fluid containers 544 (e.g., a container with a reagent) and 546 (e.g., a container with IC media) may be fluidly associated with either first fluid inlet path 542 via valves 548 and 550, respectively or second fluid inlet path 574 via valves 570 and 576. First and second sterile sealable input priming paths 508 and 509 are also provided. An air removal chamber (ARC) 556 is fluidly associated with first circulation path 502. The air removal chamber 556 may in embodiments include one or more ultrasonic sensors including an upper sensor and lower sensor to detect air, a lack of fluid, and/or a gas/fluid interface, e.g., an air/fluid interface, at certain measuring positions within the air removal chamber 556. For example, ultrasonic sensors may be used near the bottom and/or near the top of the air removal chamber 556 to detect air, fluid, and/or an air/fluid interface at these locations. Embodiments provide for the use of numerous other types of sensors without departing from the spirit and scope of the present disclosure. For example, optical sensors may be used in accordance with embodiments of the present disclosure. Air or gas purged from the CES 500 during portions of the priming sequence or other protocols can vent to the atmosphere out air valve 560 via line 558 that is fluidly associated with air removal chamber 556.

EC media (from bag 568) or wash solution (from bag 566) may be added to either the first or second fluid flow paths in embodiments. Fluid container 566 may be fluidly associated with valve 570 that is fluidly associated with first fluid circulation path 502 via distribution valve 572 and first fluid inlet path 542. Alternatively, fluid container 566 can be fluidly associated with second fluid circulation path 504 via second fluid inlet path 574 and second fluid flow path 584 by opening valve 570 and closing distribution valve 572. Likewise, fluid container 568 is fluidly associated with valve 576 that may be fluidly associated with first fluid circulation path 502 via first fluid inlet path 542 and distribution valve 572. Alternatively, fluid container 568 may be fluidly associated with second fluid inlet path 574 by opening valve 576 and closing valve distribution 572.

In the IC loop, fluid may be initially advanced by the IC inlet pump 554. In the EC loop, fluid may be initially advanced by the EC inlet pump 578. An air detector 580, such as an ultrasonic sensor, may also be associated with the EC inlet path 584.

In at least one embodiment, first and second fluid circulation paths 502 and 504 are connected to waste line 588. When valve 590 is opened, IC media can flow through waste line 588 and to waste container 586. Likewise, when valve 582 is opened, EC media can flow through waste line 588 to waste container 586.

In the embodiment shown in FIG. 5, CES 500 includes a heat exchanger 552 that may be provided to exchange heat from waste, flowing into waste container 586, to media reagent or wash solution flowing from one or more of containers 544, 546, 566, or 568.

CES 500 also includes a concentration system 599 that allows components of fluid exiting cell growth chamber 501 to be concentrated before being collected. As described in further detail below, cells grown/expanded in cell growth chamber 501 can be harvested and concentrated using concentration system 599. In other embodiments, concentration system 599 may be used to concentrate molecules, viral, or subcellular components that exit cell growth chamber 501 prior to collecting the molecules, viral or subcellular components.

Although concentration subsystem 599 is illustrated in FIG. 5 as including a number of components, it should be understood that this is merely for explanatory purposes and in other embodiments, concentration subsystem 599 may include fewer, or more, components than those shown and described with respect to FIG. 5.

In the embodiment illustrated in FIG. 5, the concentration subsystem 599 includes valves 589, 591, and 595 as well as a tangential flow filter (TFF) 587, which is used to separate components from a fluid removed from growth chamber 501. Path 585 is fluidly associated with an outlet port 583 of TFF 587. Path 579 is fluidly associated with a first outlet port 581 of TFF 587. Path 575 is fluidly associated with a second inlet port 577 of TFF 587.

As can be appreciated valves 569, 589, 591, and 595 can be operated to control the flow of fluid after the fluid exits cell growth chamber 501. In one embodiment, fluid removed from growth chamber 501, through port 501B, can be circulated back to growth chamber 501. In this embodiment, valve 591 is opened; valves 569 and 589 are closed; and pump 512 circulates the fluid exiting outlet port 501B, back to inlet port 501A and into the growth chamber 501.

In another embodiment, fluid removed from growth chamber 501 is collected after flowing out of port 501B. For example, growth chamber 501 may be used to grow/expand cells, which are then harvested. During harvesting, the cells may be removed from growth chamber 501 in a fluid, which after exiting port 501B is collected in container 567. In these embodiments, valve 569 is opened. Fluid flows from port 501B through valve 569 and into container 567.

Embodiments of the present invention also provide for concentrating a component of a fluid that exits growth chamber 501. In these embodiments, fluid from chamber 501 flows through TFF 587, which concentrates at least one component in the fluid by removing at least a second component from the fluid. In these embodiments, valves 595 and 589 are open and valves 569 and 591 are closed. Fluid flows from port 501B through into TFF 587. In TFF 587, at least a portion of a first component of the fluid is removed from the fluid, which generates two concentrated fluid components. One fluid component is concentrated with respect to the first component and the other fluid component is concentrated with respect to the remaining components. A first concentrated fluid component exits port 577 and circulates through valve 589 and back into port 583 of TFF 587, and a second concentrated fluid component exits port 581 and is collected in container 571.

In some embodiments, after the first concentrated fluid component has circulated through the TFF 587 for a predetermined amount of time, or reached a predetermined concentration in one component, valve 591 may be opened to circulate the first concentrated fluid back into growth chamber 501. In other embodiments, after the first concentrated fluid has circulated through the TFF 587 for a predetermined amount of time, valve 569 may be opened, the first concentrated fluid in container 567.

Concentration subsystem 599 allows CES 500 to be used for a number of processes. In one embodiment, CES 500 may be used to grow/expand cells. The cells may be seeded and grown within growth chamber 501. After they have expanded to a desired quantity, the cells may be harvested, but first circulated through concentration system 599 to collect a concentrated volume of cells in container 567.

In other embodiments, CES 500 may be used to generate a concentrated volume of molecules. Cells may be grown within cell growth chamber 501. As the cells grow, they may generate molecules, e.g., proteins, antibodies, cytokines, factors, virons, other cellular-produced constituents that may be useful for other processes. In one embodiment, the molecules may be useful in promoting/enhancing cell growth or for vaccine production. In these embodiments, a fluid, which may contain cells, is removed from growth chamber 501. The fluid is passed through TFF 587, where the molecules are removed from the fluid in the second fluid component collected in container 571. The remaining fluid, e.g., the first concentrated fluid component can be circulated back through the TFF 587 until a desired volume of concentrated molecules are collected in container 571.

The forgoing are merely some examples of processes in which the CES 500 and concentration subsystem 599 can be utilized. Embodiments of CES 500 and subsystem 599 are not limited to the examples described above.

It is further noted that in embodiments, various components of the CES 500 can be contained or housed within a machine or housing, such as cell expansion machine 202 (FIGS. 2 and 3), wherein the machine may control the temperature of CES 500, including any liquid, cells, or other molecules circulating in CES 500, at a relatively constant temperature.

In embodiments, the flow rates of the IC loop and EC loop in CES 500 can be adjusted to a predetermined value by controlling the speed of pumps 528 and 512. In various embodiments, the flow rate of the IC loop and EC loops can be independently set to a range of values, non-limiting examples including, about 2, about 4, about 6, about 8, about 10, about 15, about 20, about 25, about 30, about 35, about 40, about 45, about 50, about 60, about 70, about 80, about 90, about 100, about 200, about 300, about 400 or about 500 mL/minute. In embodiments of CES 500, the IC loop may be set to between about 10 to about 20 mL/minute. In embodiments, the flow rate of the EC loop should be set to allow fluid, such as media to flow through oxygenator 532 and re-establish oxygen levels. If the flow rate through the EC loop is too high, then the oxygen level in the fluid flowing through the oxygenator 532 will not be re-established. In one embodiment, the flow rate of the EC loop is between about 20 and about 30 mL per minute, which allows the oxygen levels to be reestablished.

In some embodiments, pump 554 may pump additional fluid, e.g., media, into the CES 500. In one embodiment, fluid may be added to CES 500 at a low flow rate, e.g., about 0.1 mL per minute, to replace fluid that evaporates through oxygenator 532.

As can be appreciated from the description above, CES 500 provides a closed system in which cells may be grown in the growth chamber 501 and concentrated using concentration subsystem 599, generating a concentrated volume of cells that may be utilized for therapeutic or research purposes. One feature of cells grown in CES 500 is that they are not exposed to the ambient environment and therefore have a low risk of contamination.

In other embodiments, CES 500 provides a closed system for generating molecules and other cellular products. Cells within growth chamber 501 may generate molecules such as peptides, proteins, cytokines, growth factors, virons, or other cellular products that may be collected and concentrated using concentration subsystem 599, which allows the molecules to be removed and the cells to be returned to the growth chamber 501 to generate additional molecules. The molecules can then be utilized for therapeutic or research purposes. The molecules are generated in a closed system that is not exposed to the ambient environment, which minimizes the risk of contamination.

Turning to FIG. 6, a schematic of another embodiment of a cell expansion system 600 is shown. CES 600 includes a first fluid circulation path 602 (also referred to as the "intracapillary loop" or "IC loop") and second fluid circulation path 604 (also referred to as the "extracapillary loop" or "EC loop"). First fluid flow path 606 is fluidly associated with cell growth chamber 601 to form first fluid circulation path 602. Fluid flows into cell growth chamber 601 through IC inlet port 601A, through hollow fibers in cell growth chamber 601, and exits via IC outlet port 601B. Pressure sensor 610 measures the pressure of media leaving cell growth chamber 601. In addition to pressure, sensor 610 may in embodiments also be a temperature sensor that detects the media pressure and temperature during operation. Media flows through IC circulation pump 612 which can be used to control the rate of media flow. IC circulation pump 612 may pump the fluid in a first direction or second direction opposite the first direction. Exit port 601B can be used as an inlet in the reverse direction. Media entering the IC loop may enter through valve 614. As those skilled in the art will appreciate, additional valves and/or other devices can be placed at various locations to isolate and/or measure characteristics of the media along portions of the fluid paths. Accordingly, it is to be understood that the schematic shown represents one possible configuration for various elements of the CES 600 and modifications to the schematic shown are within the scope of the one or more present embodiments.

With regard to the IC loop, samples of media can be obtained from sample coil 618 during operation. Media then returns to IC inlet port 601A to complete fluid circulation path 602. Cells grown/expanded in cell growth chamber 601 can be flushed out of cell growth chamber 601 into harvest bag 667 through valve 669 and line 697. Alternatively, when valve 669 is closed, the cells may be redistributed within chamber 601 for further growth.

Fluid in second fluid circulation path 604 enters cell growth chamber 601 via EC inlet port 601C, and leaves cell growth chamber 601 via EC outlet port 601D. Media in the EC loop is in contact with the outside of the hollow fibers in the cell growth chamber 601, thereby allowing diffusion of small molecules into and out of the hollow fibers that may be within chamber 601.

Pressure/temperature sensor 624 disposed in the second fluid circulation path 604 allows the pressure and temperature of media to be measured before the media enters the EC space of the cell growth chamber 601. Sensor 626 allows the pressure and temperature of media in the second fluid circulation path 604 to be measured after it leaves the cell growth chamber 601. With regard to the EC loop, samples of media can be obtained from sample port 630 or a sample coil during operation.

After leaving EC outlet port 601D of cell growth chamber 601, fluid in second fluid circulation path 604 passes through EC circulation pump 628 to gas transfer module 632. EC circulation pump 628 may also pump the fluid in opposing directions. Second fluid flow path 622 is fluidly associated with gas transfer module 632 via an inlet port 632A and an outlet port 632B of gas transfer module 632. In operation, fluid media flows into gas transfer module 632 via inlet port 632A, and exits gas transfer module 632 via outlet port 632B. Gas transfer module 632 adds oxygen or other gasses/gas mixtures to media in the CES 600. In various embodiments, media in second fluid circulation path 604 is in equilibrium with gas entering gas transfer module 632. The gas transfer module 632 can be any appropriately sized device known in the art and useful for oxygenation or gas transfer. Air or gas flows into gas transfer module 632 via filter 638 and out of oxygenator or gas transfer device 632 through filter 640. Filters 638 and 640 reduce or prevent contamination of oxygenator 632 and associated media. Air or gas purged from the CES 600 during portions of a priming sequence can vent to the atmosphere via the gas transfer module 632.

In the configuration depicted for CES 600, fluid media in first fluid circulation path 602 and second fluid circulation path 604 flows through cell growth chamber 601 in the same direction (a co-current configuration). The CES 600 can also be configured to flow in a counter-current conformation.

In accordance with at least one embodiment, media, including cells (from a source such as a cell container, e.g. a bag) can be attached at attachment point 662, and fluid media from a media source can be attached at attachment point 646. The cells and media can be introduced into first fluid circulation path 602 via first fluid flow path 606. Attachment point 662 is fluidly associated with the first fluid flow path 606 via valve 664, and attachment point 646 is fluidly associated with the first fluid flow path 606 via valve 650. A reagent source may be fluidly connected to point 644 and be associated with fluid inlet path 642 via valve 648, or second fluid inlet path 674 via valves 648 and 672.

Air removal chamber (ARC) 656 is fluidly associated with first circulation path 602. The air removal chamber 656 may include one or more sensors including an upper sensor and lower sensor to detect air, a lack of fluid, and/or a gas/fluid interface, e.g., an air/fluid interface, at certain measuring positions within the air removal chamber 656. For example, ultrasonic sensors may be used near the bottom and/or near the top of the air removal chamber 656 to detect air, fluid, and/or an air/fluid interface at these locations. Embodiments provide for the use of numerous other types of sensors without departing from the spirit and scope of the present disclosure. For example, optical sensors or Raman spectroscopy based sensors may be used in accordance with embodiments of the present disclosure. Air or gas purged from the CES 600 during portions of the priming sequence or other protocols can vent to the atmosphere out air valve 660 via line 658 that is fluidly associated with air removal chamber 656.

An EC media source may be attached to EC media attachment point 668 and a wash solution source may be attached to wash solution attachment point 666, to add EC media and/or wash solution to either the first or second fluid flow path. Attachment point 666 may be fluidly associated with valve 670 that is fluidly associated with first fluid circulation path 602 via valve 672 and first fluid inlet path 642. Alternatively, attachment point 666 can be fluidly associated with second fluid circulation path 604 via second fluid inlet path 674 and second fluid flow path 684 by opening valve 670 and closing valve 672. Likewise, attachment point 668 is fluidly associated with valve 676 that may be fluidly associated with first fluid circulation path 602 via first fluid inlet path 642 and valve 672. Alternatively, fluid container 668 may be fluidly associated with second fluid inlet path 674 by opening valve 676 and closing valve distribution 672.

In the IC loop, fluid may be initially advanced by the IC inlet pump 654. In the EC loop, fluid is initially advanced by the EC inlet pump 678. An air detector 680, such as an ultrasonic sensor, may also be associated with the EC inlet path 684.

In at least one embodiment, first and second fluid circulation paths 602 and 604 are connected to waste line 688. When valve 690 is opened, IC media can flow through waste line 688 and to waste bag 686. Likewise, when valve 692 is opened, EC media can flow to waste bag 686.

After cells have been grown in cell growth chamber 601, they may be harvested via cell harvest path 697. Here, cells from cell growth chamber 601 can be harvested by pumping the IC media containing the cells through cell harvest path 697, with valve 669 open, into cell harvest bag 667.

In addition to the other components described above, CES 600 also includes a secondary IC loop 699, which may also be referred to as a concentration subsystem. Secondary IC loop 699 includes a tangential flow filter 687 (TFF) and valves 695, 689, and 691. As described in greater detail below, the components of CES 600 can be operated during various procedures to generate a concentrated fluid component and a concentrated cell component from a fluid containing expanded cells. In embodiments, the expanded cells may have been grown in cell growth chamber 601. Once expanded, the cells may be moved from cell growth chamber 601 and directed to loop 699 and across TFF 687. In some embodiments, loop 699 includes multiple flow control devices, in addition to valves 695, 691, and 689, and TFF 687.

As can be appreciated, in some embodiments, cells expanded in a cell growth chamber (such as a bioreactor) may generate compounds and/or molecules, e.g., proteins, antibodies, factors, other cellular-produced constituents etc., that are useful in various applications. In order to harvest the compounds, subcellular components, virons and/or molecules, fluid circulating in a cell growth chamber can be flowed into a tangential flow filter such as TFF 687. The TFF 687 may be configured to allow the compounds and/or molecules from the fluid to be removed. The remaining components, including any cells, can be recirculated into the cell growth chamber. CES 600 may be used in embodiments to continuously harvest compounds and/or molecules from fluid circulated through the cell growth chamber 601.

In other embodiments, it is desirable to generate a volume of concentrated cells that have been expanded. CES 600 provides a closed system that allows cells to be expanded and also concentrated without being exposed to ambient air, which may contaminate the cells. Cells that are expanded in the cell growth chamber 601 can be carried by a fluid stream into loop 699 and across TFF 687. TFF 687 can separate liquid in the fluid, compounds, and molecules from the cells, generating a concentrated fluid component (with liquid, compounds, and molecules) and a concentrated cell component (with liquid and cells). The concentrated cell component can be recirculated to TFF 687 (within loop 699) until a desired concentration of cells is achieved in the concentrated cell component. The concentrated cell component can then be collected and removed from CES 600. CES 600 therefore allows cells to be expanded and concentrated in a single closed system.

It is noted that portions of CES 600 may be part of a detachable flow circuit. For example, loop 699 and TFF 687 may be part of a detachable flow circuit that includes the IC loop, the EC loop, and other flow paths of CES 600.

Below are descriptions of valve and pump states of components of CES 600 during various procedures performed using the secondary IC loop 699 in CES 600, according to some embodiments. It is noted that the following is provided for illustrative purposes only, and involve steps, features, and components that are part of embodiments of the present invention. The description below is not intended to describe essential characteristics or limit other embodiments of the present invention.

As noted above, embodiments may generate a volume of concentrated cells. The cells begin in suspension throughout the entire IC loop, e.g., 602. In some embodiments, a bag of phosphate buffered saline (PBS) is connected to attachment points 662 and 668. Fluid flows through path 602, through inlet port 601A of cell growth chamber 601 and out of outlet port 601B and into loop 699 containing the TFF 687. Once the cells are within loop 699, pump 612 circulates the fluid within the loop 699 during a concentration process, namely the fluid is circulated through TFF 687 and valve 689, and then through inlet port 677 of TFF 687. In embodiments, valves 691 and 669 are closed and valve 689 is opened. Excess fluid is expelled via second outlet port 681 of TFF 687 and collected in container 671. A concentrated cellular component exists TFF 687 through first outlet port 683. The following states of CES 600 may result in an appropriate fluid flow path for embodiments of this process:

Pump 654: on;
Pump 612: on, clockwise;
Pump 678: on;
Pump 628: on, clockwise;
Valve 664: open;
Valve 650: closed;
Valve 648: closed;
Valve 695: open;
Valve 691: closed;
Valve 689: open;
Valve 660: closed;
Valve 614: open;
Valve 669: closed;
Valve 690: closed;
Valve 692: closed;
Valve 670: open;
Valve 672: closed; and
Valve 676: open.

In embodiments, some cells may remain in the line between the air removal chamber 656 and valve 691. In order to move these cells into loop 699, the cells are moved into loop 699 by introducing fluid directly into the loop 699 from the air removal chamber 656. As noted above, any excess fluid in loop 699 is separated by TFF 687 and collected into container 671. The following states of CES 600 may result in an appropriate fluid flow path for embodiments of this process:

Pump 654: on;
Pump 612: on, counter-clockwise;
Pump 678: off;
Pump 628: on, clockwise;
Valve 664: open;
Valve 650: closed;
Valve 648: closed;
Valve 695: open;
Valve 691: open;
Valve 689: open;
Valve 660: closed;
Valve 614: closed;
Valve 669: closed;
Valve 690: closed;
Valve 692: open;
Valve 670: open;
Valve 672: closed; and
Valve 676: closed.

In some embodiments, cells in loop 699 may be conditioned. The cells begin in suspension throughout the entire IC loop, e.g., 602. In some embodiments, a bag of phosphate buffered saline (PBS) is connected to attachment points 662 and 668. In embodiments, complete media is connected to attachment point 644. Cells may be released from their attachment to growth chamber 601 using trypsin or cellular release biomolecule in the fluid circulated in the chamber 601. This reagent may be neutralized by protein, in embodiments, after removing the cells from the cell growth chamber 601. This can be accomplished, in embodiments, by introducing complete media (base media plus protein (e.g., Fetal Bovine Serum) directly into loop 699 from the air removal chamber 656. Excess fluid coming into loop 699 is expelled via TFF 687 and collected into container 671. The following states of CES 600 may result in an appropriate fluid flow path for embodiments of this process:

Pump 654: on;
Pump 612: on, counter-clockwise;
Pump 678: off;
Pump 628: on, clockwise;
Valve 664: closed;
Valve 650: closed;
Valve 648: open;
Valve 695: open;
Valve 691: open;
Valve 689: open;
Valve 660: closed;
Valve 614: closed;
Valve 669: closed;
Valve 690: closed;
Valve 692: open;
Valve 670: open;
Valve 672: closed; and
Valve 676: closed.

In other embodiments, the fluid containing trypsin or other cellular release biomolecule may be diluted to levels that may not be harmful to cells as opposed to neutralizing with protein. Rather than using complete media connected to attachment point 644, PBS (more cost effective than complete media) may be connected to attachment point 662. Cells can be washed multiple times or continuously washed using a configurable volume and the above described state for CES 600 (the state of valves 664, 650, or 648 may be changed depending on the location of the desired wash/condition fluid). In embodiments, cells can be conditioned for later processing (e.g. cryopreservation, administered to patient, etc.) by flowing a desired fluid into the loop 699. For example, using approximately 3× the volume of loop 699 plus the volume of air removal chamber 656 (3× volume exchange=~95% complete exchange) and using the above described states of CES 600 (the state of valves 664, 650, or 648 may be changed depending on the location of the desired conditioning fluid).

To collect the concentrated cells, in embodiments, the cells may be in suspension throughout the entire loop 699. In some embodiments, a bag of phosphate buffered saline (PBS) or other cell stabilizing fluid is connected to attachment points 662 and 668. In embodiments, complete media is connected to attachment point 644. Fluid used to condition cells in preparation for harvest may be connected to attachment point 646. Conditioned cells may be harvested from loop 699 by directing the same fluid used for cell conditioning through the loop 699 and TFF 687 and collected in container 667. The following states of CES 600 may result in the proper fluid flow path:

Pump 654: on;
Pump 612: on, clockwise;
Pump 678: off;
Pump 628: on, clockwise;
Valve 664: closed;
Valve 650: open;
Valve 648: closed;
Valve 695: closed;
Valve 691: open;
Valve 689: open;
Valve 660: closed;
Valve 614: closed;
Valve 669: open;
Valve 690: closed;
Valve 692: open;
Valve 670: open;
Valve 672: closed; and
Valve 676: open.

In some embodiments, a 1.5× volume exchange of the TFF 687 plus the volume of the air removal chamber will be sufficient to harvest >95% of the cells contained within loop 699.

In embodiments, the cells may be in suspension throughout the entire loop 699. It may be desirable to collect only a portion of the cells. In these embodiments, a bag of phosphate buffered saline (PBS) is connected to attachment points 662 and 668. In embodiments, the loop 699 can be divided into two (2) individual volumes. The first volume (V2A) is the volume contained between point B and point A that includes pump 612. The second volume (V2B) is the volume between Point A and Point B containing the TFF 687. In the case when cells are evenly concentrated in the fluid of the loop 699, the concentration of cells can be reduced by the proportion (V2A/(V2A+V2B)). This is accomplished by circulating the primary IC loop for a volume equal to or greater than V2A. The number of times this process can be repeated and behave as described above is limited by the expression (V1B/V1A); where V1A=volume of the primary IC loop between Point A and Point B containing Pump 1 and V1B is the volume of the primary IC loop between Point A and Point B containing the cell growth chamber. The following states of CES 600 may result in the proper fluid flow path:

Pump 654: off;
Pump 612: on, counter-clockwise;
Pump 678: on;
Pump 628: on, clockwise;
Valve 664: closed;
Valve 650: closed;
Valve 648: closed;
Valve 695: closed;
Valve 691: open;
Valve 689: closed;
Valve 660: closed;
Valve 614: open;
Valve 669: closed;
Valve 690: closed;
Valve 692: open;
Valve 670: open;
Valve 672: closed; and
Valve 676: open.

The above step may be useful for harvesting a portion of cells in the loop 699, and then returning the remaining portion to the bioreactor. For example, the remaining portion can be directed back into the bioreactor as part of a reseeding step.

In order to reestablish even concentration of cells in the loop 699 after performing the above step, the following states may result in the proper fluid flow path:

Pump 654: off;
Pump 612: on, counter-clockwise;
Pump 678: on;
Pump 628: on, clockwise;
Valve 664: closed;
Valve 650: closed;
Valve 648: closed;
Valve 695: closed;
Valve 691: closed;
Valve 689: open;
Valve 660: closed;
Valve 614: closed;
Valve 669: closed;
Valve 690: closed;
Valve 692: open;
Valve 670: open;
Valve 672: closed; and
Valve 676: open.

Among other features, CES 600 provides a closed system in which cells may be grown in a cell growth chamber 601 and concentrated using loop 699, to generate a concentrated volume of cells that may be utilized for therapeutic or research purposes. The cells are grown in CES 600 in a closed environment that is not exposed to the ambient environment, and therefore the system has a low risk of contamination. The risk of contamination is lower than with other process that utilize flasks for growing cells, which are exposed to the ambient environment. After the cells are grown, they must be transferred to a separate system for concentrating the cells, which exposes them once again to possible contamination. The exposure to contamination is significantly reduced in CES 600.

CES 600 also provides a closed system for generating molecules, virons, and/or other cellular products. Cells within growth chamber 601 may generate molecules such as proteins, cytokines, growth factors, or other cellular products that may be collected and concentrated using loop 699, which allows the molecules to be removed and the cells to be returned to the growth chamber 601 to generate additional molecules. The molecules can then be utilized for therapeutic or research purposes. The molecules are generated in a closed system that is not exposed to the ambient environment, which minimizes the risk of contamination.

It is noted that in embodiments, components of the CES 600 may be contained or housed within a machine or housing, such as cell expansion machine 202 (FIGS. 2 and 3), wherein the machine maintains CES 600, including any cells, fluid (e.g., media) at a predetermined temperature. It is further noted that in embodiments, components of CES 600 may be combined with components of CES 500 (FIG. 5). As one example, CES 600 may include a heat exchanger in some embodiments, such as heat exchanger 552, described with respect to CES 500. In other embodiments, a CES may include fewer components than shown in FIGS. 5 and 6 and still be within the scope of the present disclosure.

Figure 7:
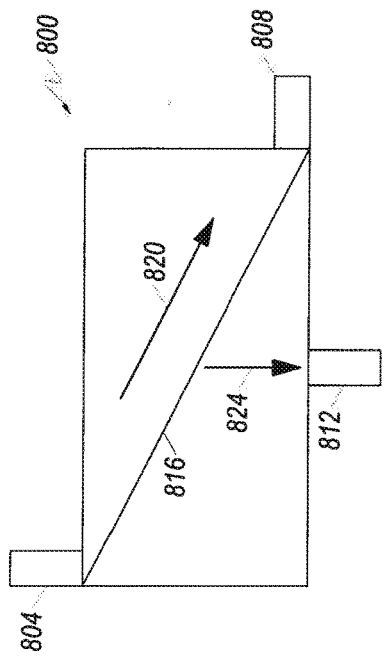
FIG. 7 illustrates a tangential flow filter design that may be used with embodiments of the present disclosure.
Figure 8:
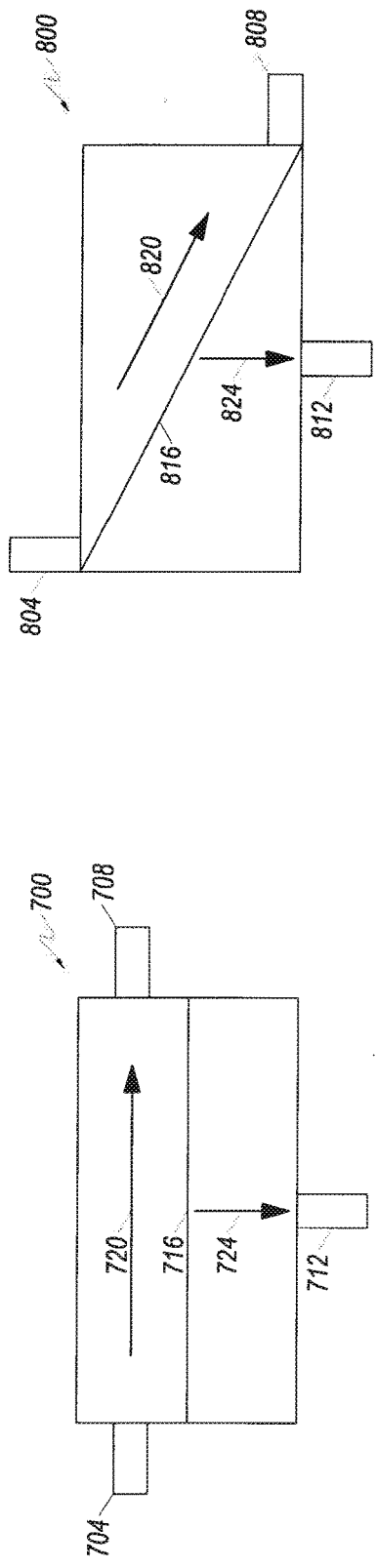
FIG. 8 illustrates another tangential flow filter design that may be used with embodiments of the present disclosure.
Figure 9:
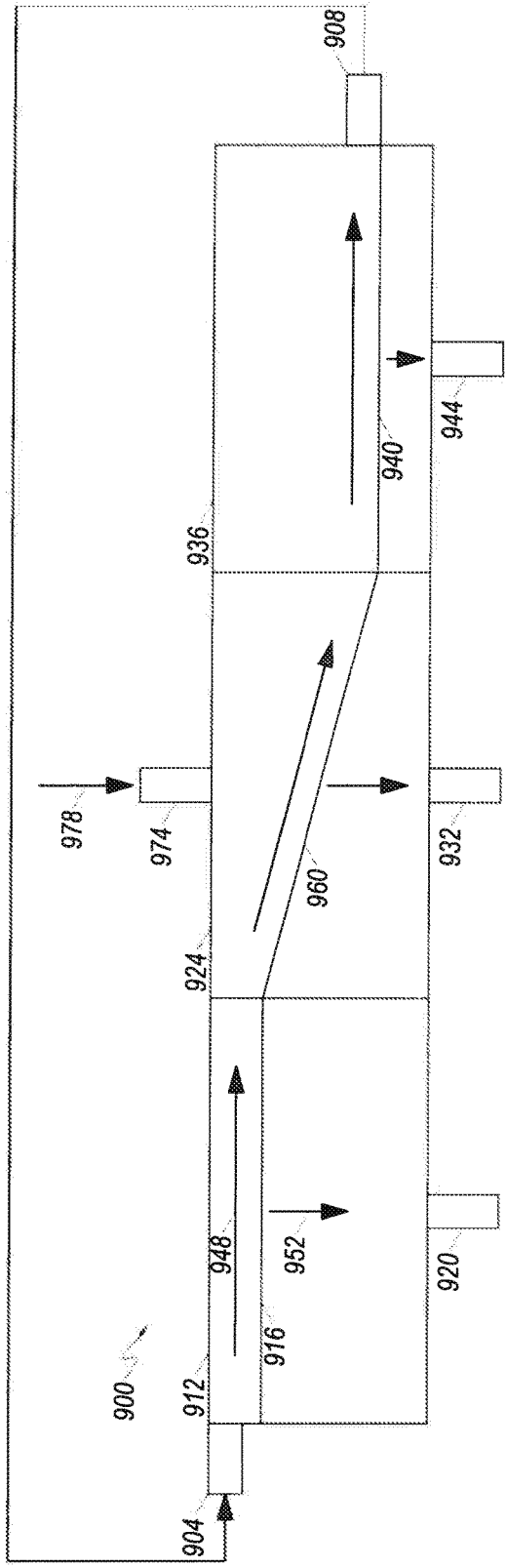
FIG. 9 illustrates yet another tangential flow filter design that may be used with embodiments of the present disclosure.

FIGS. 7-9 illustrate embodiments of tangential flow filters (TFFs). It is noted that in some embodiments the TFFs illustrated in FIGS. 7-9 may be utilized as part of CES 500 (as TFF 587) or as part of CES 600 (as TFF 687). Also, although specific features of the TFFs are described, this is done merely for explanatory purposes, and embodiments are not limited to the description provided.

FIG. 7 illustrates a TFF 700, which includes an input port 704, a first output port 708, a second output port 712, and a membrane 716. Fluid enters TFF 700 through input port 704 in the direction indicated by arrow 720. As the fluid flows across a top surface of membrane 716, a component of the fluid passes through the membrane 716, as shown by arrow 724, and exits through second output port 712. The remaining fluid exits through first output port 708.

Membrane 716 is, in embodiments, made from a porous material that allows at least one component of a fluid to pass through. In some embodiments, membrane 716 is selected for a specific component of a fluid to pass through, while in other embodiments, membrane 716 may be selected to prevent a component from passing through. For example, TFF 700 may be used as part of a closed cell expansion system (e.g., CES 500 and 600). The cells may be grown and used to generate a molecule for collection and use in a subsequent therapeutic or research process. In this embodiment, the membrane 716 may be selected with a pore size that will allow the molecule to pass through and flow out of the second output port 712. In other embodiments, the membrane 716 may be selected to concentrate cells by allowing other components of a fluid to pass through the membrane.

FIG. 8 illustrates another tangential flow filter (TFF) 800, which includes an inlet port 804, a first outlet port 808, a second outlet port 812, and a membrane 816. Similar to TFF 700, fluid enters TFF 800 through input port 804 in the direction indicated by arrow 820. As the fluid flows across membrane 816, a component of the fluid passes through the membrane 816, as shown by arrow 824, and exits through second output port 812. The remaining fluid exits through first output port 808. While membrane 716 of TFF 700 is substantially horizontal, membrane 816 is positioned at an angle with respect to a horizontal position. This difference allows gravity to assist in flowing the fluid across the top surface of the membrane 816. In embodiments, membrane 816 may be positioned at various angles with respect to horizontal such as, without limitation, about 5 degrees, about 10 degrees, about 15 degrees, about 20 degrees, about 25 degrees, about 30 degrees, about 35 degrees, about 40 degrees, or about 45 degrees. These are merely some non-limiting examples, and in other embodiments, the membrane 816 may be positioned at an angle with respect to horizontal that is less than about 80 degrees, less than about 75 degrees, less than about 70 degrees, less than about 65 degrees, less than about 60 degrees, less than about 55 degrees, less than about 50 degrees, less than about 45 degrees, less than about 40 degrees, less than about 35 degrees or less than about 30 degrees.

In some embodiments, a TFF may have different chambers, each with different characteristics. For example, FIG. 9 illustrates a TFF 900 which includes multiple chambers. TFF 900 includes an input port 904, and a fourth output port 908. In addition, TFF 900 includes a first chamber 912 with a first membrane 916 and a first outlet port 920. A second chamber 924 of TFF 900 includes a second membrane 960 and a second output port 932. A third chamber 936 of TFF 900 includes a third membrane 940 and a third output port 944.

In embodiments, a fluid enters TFF 900 through inlet port 904, and flows through chamber 912 in the direction of arrow 948. As the fluid passes across a top surface of membrane 916, a first component of the fluid passes through membrane 916, as shown by arrow 952 and out of first output port 920. The remaining fluid enters chamber 924 and passes across the top surface of membrane 960. A second component of the fluid passes through membrane 960 and out of second output port 932. The remaining fluid flows into chamber 936 and passes across a top surface of membrane 940. A third component of the fluid passes through membrane 940 and out of second output port 944. The remaining fluid then exits TFF 900 through fourth output port 908. In embodiments, TFF 900 may be part of a system that circulates fluid exiting fourth output port 908 back to inlet port 904 so the fluid can flow through TFF 900 more than one once.

As can be appreciated TFF 900 may be useful in removing a large amount of a component from a fluid. For example, membranes, 916, 960, and 940 may all be selected to remove a particular component, e.g., the same component, from a liquid flowing through TFF 900. A first portion of the component may be removed in chamber 912, a second portion may be removed in chamber 924, and a third portion of the same component may be removed in chamber 936. In this embodiment, the fluid will be significantly reduced in the component by the time it exits output port 908. In one example, if the fluid has been circulated through a cell growth chamber and includes cells and cellular products, TFF 900 may be designed to concentrate the cells in the fluid. Accordingly, 916, 960, and 940 may be selected to allow liquid and smaller molecules, but not cells, to pass through.

In other embodiments, membranes 916, 960, and 940 may each be selected to allow a different component to pass through. In these embodiments, each of membranes 916, 960, and 940 may be designed, e.g., material, pore size, thickness, hydrophobicity, etc. to remove a specific component from the fluid. For example, TFF 900 may be used to remove different molecules, e.g., cytokines, growth factors, other cellular products, from fluid circulated through a cell growth chamber or other cell growth chamber. Each of the different molecules may be removed from the fluid separately. The molecules can then each be separately collected and later utilized in other processes such as therapeutic or research processes.

TFFs used in some embodiments may allow for fluids, and components within fluids to be conditioned as they flow through the TFF. In one embodiment, TFF 900 includes an additional input port 974 into which another material maybe introduced into TFF 900, as shown by arrow 978. The material may be used to condition one or more components of the fluid. For example, if the fluid includes components that may have a negative effect on other components in the fluid, the material added through port 974 may neutralize the affect. In other embodiments, the material may be added to prepare the fluid for further processing.

In one embodiment, a fluid that includes cells as well as cellular products is passed through TFF 900 to concentrate the cells and remove other components. In some embodiments, the fluid may contain tripsin, which may affect the viability of the cells if left in the fluid for a long period of time. In this embodiment, a material, e.g., a protein may be added through port 974 in order to neutralize the tripsin.

Accordingly, in this embodiment, flowing the fluid through TFF 900 increases the concentration of cells in the fluid, because components of the fluid pass through membranes 916, 960, and 940, and the cells are conditioned by the addition of protein.

In another embodiment, the fluid that includes cells as well as cellular products is passed through TFF 900 to concentrate the cells. In some embodiments, the cells may be subjected to cryopreservation after passing through TFF 900. In this embodiment, a cryoprotectant, e.g., a glycol, may be added through port 974 in order to condition the cells for later freezing. Accordingly, in this embodiment, circulating the fluid through TFF 900 increases the concentration of cells in the fluid, because components of the fluid pass through membranes 916, 960, and 940, and the cells are conditioned by the addition of the cryoprotectant.

In embodiments, one or more of membranes 916, 960, and 940 may have characteristics that are selective for allowing cells, subcellular components, virons and/or macromolecules smaller than about 100 nanometers in diameter to pass through. Components of a fluid passing across the membrane surface, smaller than about 100 nanometers, will pass through the membrane while larger molecules and particles are retained. In other embodiments, one or more of membranes 916, 960, and 940 may have characteristics that are selective for allowing components that are smaller or equal to about 500 nanometers, about 450 nanometers, about 400 nanometers, about 350 nanometers, about 300 nanometers, about 250 nanometers, about 200 nanometers, or about 150 nanometers, to pass through. In other embodiments, one or more of membranes 916, 960, and 940 may have characteristics that are selective for preventing components that are larger than or equal to about 50 nanometers, about 55 nanometers, about 60 nanometers, about 65 nanometers, about 70 nanometers, about 75 nanometers, about 80 nanometers, about 85 nanometers, about 90 nanometers, about 95 nanometers, or about 100 nanometers, from passing through. These are merely some examples, and one or more of membranes 916, 960, and 940 may be selective for different size components in a fluid.

It is noted that the flow rate of a fluid through one or more of membranes 916, 960, and 940 will depend on a number of factor, including the characteristic of membranes 916, 960, and 940, as well as the flow rate of the fluid through TFF 900. In one embodiment the flow rate may be greater than about 50 mL/min of trans-membrane fluid flow. In other embodiments, the flow rate may be greater than about 100 mL/min, about 150 mL/min, about 200 mL/min, about 250 mL/min, about 300 mL/min, about 350 mL/min, about 400 mL/min, about 450 mL/min, about 500 mL/min, or about 550 mL/min.

FIG. 10 illustrates a hollow fiber membrane device 1000 that may be used in some embodiments, as a TFF (e.g., TFF 587, TFF 687, TFF 700, TFF 800, or TFF 900) or as a cell growth chamber (124, 298 501, or 601). Hollow fiber membrane device 1000 includes a number of hollow fibers 1022. FIG. 10 depicts a cut-away side view of the hollow fiber membrane device 1000. Hollow fiber membrane device 1000 is bounded by hollow fiber membrane housing 1002. Hollow fiber membrane housing 1002 further includes four openings, or ports: inlet port 1004, outlet port 1006, inlet port 1008, and outlet port 1010.

Fluid may enter hollow fiber membrane device 1000 through inlet port 1004, pass into and through the inside of a number of hollow fibers (referred to in various embodiments as the intracapillary ("IC") side or "IC space" of the hollow fiber membrane), and out of hollow fiber membrane device 1000 through outlet port 1006, creating a first circulation path 1018. The terms "hollow fiber," "hollow fiber capillary," and "capillary" may be used herein interchangeably. A plurality of hollow fibers may be collectively referred to as a "membrane." Fluid in a second circulation path 1020 flows in the hollow fiber membrane device through inlet port 1008, comes in contact with the outside of the hollow fibers (referred to as the "EC side" or "EC space" of the membrane), and exits hollow fiber membrane device 1000 via outlet port 1010. In embodiment where hollow fiber membrane device 1000 is used to grow cells, the cells can be contained within the IC side or EC side of the membrane.

Although hollow fiber membrane device 1000 is depicted as cylindrical in shape, it can have any other shape known in the art. Hollow fiber membrane housing 1002 can be made of any type of polymeric material. In embodiments, the housing 1002 may differ in shape and size.

The ends of hollow fibers can be potted to the sides of the hollow fiber membrane device 1000 by a connective material (also referred to herein as "potting" or "potting material"). The potting can be any suitable material for binding the hollow fibers 1012, provided that the flow of fluid (e.g., media and cells or fluid with components to be removed) into the hollow fibers is not obstructed and that fluid flowing into the hollow fiber membrane device 1000 through the IC inlet port flows only into the hollow fibers. Exemplary potting materials include, but are not limited to, polyurethane or other suitable binding or adhesive components. In various embodiments, the hollow fibers and potting may be cut through perpendicular to the central axis of the hollow fibers at each end to permit fluid flow into and out of the IC side. End caps 1014 and 1016 are disposed at the end of the hollow fiber membrane device 1000.

Fluid may entering hollow fiber membrane device 1000 via inlet port 1008 and be in contact with the outside of the hollow fibers. This portion of the hollow fiber membrane device 1000 is referred to as the "extracapillary (EC) space." Molecules (e.g. water, oxygen, lactate, proteins, cellular products, etc.) can diffuse through the hollow fibers from the interior of the hollow fiber to the EC space, or from the EC space to the IC space. In embodiments in which cells are grown in the IC space, the EC space is used as a medium reservoir to supply nutrients to the cells and remove the byproducts of cellular metabolism. The media may be replaced as needed. Media may also be circulated through an oxygenator to exchange gasses as needed. In embodiments in which the hollow fiber membrane device 1000 is used as a TFF, a fluid may be flowed through the IC space and a first component of the fluid may diffuse through the fibers into the EC space where it is collected. The hollow fiber membrane device 1000 thus, in these embodiments, creates two concentrated fluids, one concentrated in the first component the other concentrated in the other components.

In various embodiments, the inner diameter of the hollow fibers can be greater than or equal to about 10000, about 9000, about 8000, about 7000, about 6000, about 5000, about 4000, about 3000, about 2000, about 1000, about 900, about 800, about 700, about 650, about 600, about 550, about 500, about 450, about 400, about 350, about 300, about 250, about 200, about 150, or about 100 microns. Likewise, the outer diameter of the hollow fiber can be, in embodiments less than or equal to about 10000, about 9000, about 8000, about 7000, about 6000, about 5000, about 4000, about 3000, about 2000, about 1000, about 900, about 800, about 700, about 650, about 700, about 650, about 600, about 550, about 500, about 450, about 400, about 350, about 300, about 250, about 200, about 150, or about 100 microns. The hollow fiber wall thickness is in embodiments sufficient to allow diffusion of the necessary molecules.

Any number of hollow fibers can be used, provided the hollow fibers can be fluidly associated with the inlet and outlet ports of the hollow fiber membrane device 1000. In various embodiments, the hollow fiber membrane device 1000 can include a number of hollow fibers greater than or equal to about 1000, about 2000, about 3000, about 4000, about 5000, about 6000, about 7000, about 8000, about 9000, about 10000, about 11000 or about 12000. In other embodiments, the hollow fiber membrane device 1000 can include a number of hollow fibers less than or equal to about 12000, about 11000, about 10000, about 9000, about 8000, about 7000, about 6000, about 5000, about 4000, about 3000, or about 2000. In other various embodiments, the length of the hollow fibers can be greater than or equal to about 100, about 200, about 300, about 400, about 500, about 600, about 700, about 800, or about 900 millimeters. In some embodiments, the cell growth chamber contains about 9000 hollow fibers that have an average length of about 295 mm, an average inner diameter of about 215 microns, and an average outer diameter of about 315 microns.

Hollow fibers can be constructed of any material capable of forming a size sufficient to form fibers capable of transporting fluid from the hollow fiber membrane device 1000 inlet ports to the outlet ports. In some embodiments, the hollow fibers can be constructed from polymeric materials capable of binding to certain types of cells, such as adherent stem cells (e.g. MSCs), when hollow fiber membrane device 1000 is being used as a cell growth chamber. In other embodiments, hollow fibers can be treated with compounds such as fibronectin to form cell adherent surfaces.

In embodiments, the hollow fibers may be made of a semi-permeable, biocompatible polymeric material. The polymeric material may include polyamide, polyarylethersulfone, polyvinylpyrrolidone, and combination thereof, such as "PA/PAES/PVP". The semi-permeable material allows transfer of nutrients, waste and dissolved gases through the membrane between the EC space and IC space when the hollow fiber membrane device 1000 is being used to grow cells. The semi-permeable material allows transfer of specific molecules or other components of a fluid through the membrane between the EC space and IC space when the hollow fiber membrane device 1000 is being used as a TFF.

In some embodiments when the hollow fiber membrane device 1000 is being used to grow cells, the hollow fibers may be characterized by a homogenous and open pore structure with a defined surface roughness. The openings of the pores may be in the size range of 0.5-3 microns, and the number of pores on the outer surface of the fibers may be in the range of 10,000 to 150,000 pores per $mm^2$. This outer layer may have thickness of about 1 to 10 microns, in some embodiments. A subsequent layer in each hollow fiber may have a sponge structure, in some embodiments. In some embodiments, the sponge structure may have a thickness of between about 1 to 15 microns. This second layer may serve as a support for the outer layer. A third layer next to the second layer, in some embodiments, has the form of finger-like structures. This third layer may provide mechanical stability and a high void volume which gives the membrane a low resistance to transporting molecules through the membrane. During use, the finger-like voids may be filled with fluid and the fluid may give a lower resistance for diffusion and convection than a matrix with a sponge-filled structure having a lower void volume. This third layer may have a thickness of 20 to 60 microns, in some embodiments.

In embodiments, the fibers of the hollow fiber membrane device 1000 may include from about 65% to about 95% by weight of at least a hydrophobic polymer and from about 5% to about 35% by weight of at least a hydrophilic polymer. Examples of hydrophobic polymers that may be included in some embodiments include, without limitation, polyamide (PA), polyaramide (PAA), polyarylethersulphone (PAES), polyethersulphone (PES), polysulphone (PSU), polyarylsulphone (PASU), polycarbonate (PC), polyether, polyurethane (PUR), polyetherimide and copolymer mixtures of any of the above polymers, such as polyethersulphone or a mix of polyarylethersulphone and polyamide. Examples of hydrophilic polymers that may be used in some embodiments include chosen from the group consisting of polyvinylpyrrolidone (PVP), polyethylene glycol (PEG), polyglycol-monoester, water soluble cellulosic derivates, polysorbate and polyethylene-polypropylene oxide copolymers.

In embodiments, when hollow fiber membrane device 1000 is used as a TFF, the hollow fibers may have characteristics that are selective for allowing cells, subcellular components, virons and/or macromolecules smaller than about 100 nanometers in diameter to pass through the fiber wall. Components of a fluid passing across the membrane surface, smaller than about 100 nanometers, will pass through the membrane while larger molecules and particles are retained. In other embodiments, the fibers may have characteristics that are selective for allowing components that are smaller or equal to about 500 nanometers, about 450 nanometers, about 400 nanometers, about 350 nanometers, about 300 nanometers, about 250 nanometers, about 200 nanometers, or about 150 nanometers, to pass through the fiber wall. In other embodiments, the fibers may have characteristics that are selective for preventing components that are larger than or equal to about 50 nanometers, about 55 nanometers, about 60 nanometers, about 65 nanometers, about 70 nanometers, about 75 nanometers, about 80 nanometers, about 85 nanometers, about 90 nanometers, about 95 nanometers, or about 100 nanometers, from passing through the fiber wall. These are merely some examples, and the fibers may be selective for different size components in a fluid.

As described above with respect to FIGS. 5 and 6, CES systems 500 and 600 may also include a second fluid flow path passing through the extracapillary space of a cell growth chamber. The second fluid flow path may be fluidly associated with an oxygenator or gas transfer module. In embodiments, a CES system may utilize three hollow fiber membrane devices, as described above with respect to FIG. 10. A first hollow fiber membrane device may be used as the oxygenator/gas transfer module, a second may be used as the cell growth chamber, and a third may be used as the TFF. In these embodiments, the hollow fiber membrane devices may have the same, or may have different, characteristics, such as pore size, fiber size, volume, surface area, etc. The fiber membrane devices used in an oxygenator/gas transfer devices, as a cell growth chamber, or TFF may be selected depending on the application. For example, in one application, such as for concentrating cells, the hollow fiber membrane device used as a TFF may be selected with a different pore size, surface area, volume, etc. than when the TFF is used to harvest cellular-produced constituents, e.g., cytokines, growth factors, etc.

While various example embodiments of cell expansion systems, components, and methods for have been described above, FIGS. 11 and 12 illustrates example operational steps for processes of concentrating components of a fluid that has circulated through a cell growth chamber, in accordance with embodiments of the present disclosure. Although specific parts of cells expansion systems may be mentioned below in describing the processes illustrated by flow diagrams 1100 and 1200, these processes are not limited to any particular system or components of system, but may be performed using other systems, components, or devices not mentioned herein.

Figure 11:
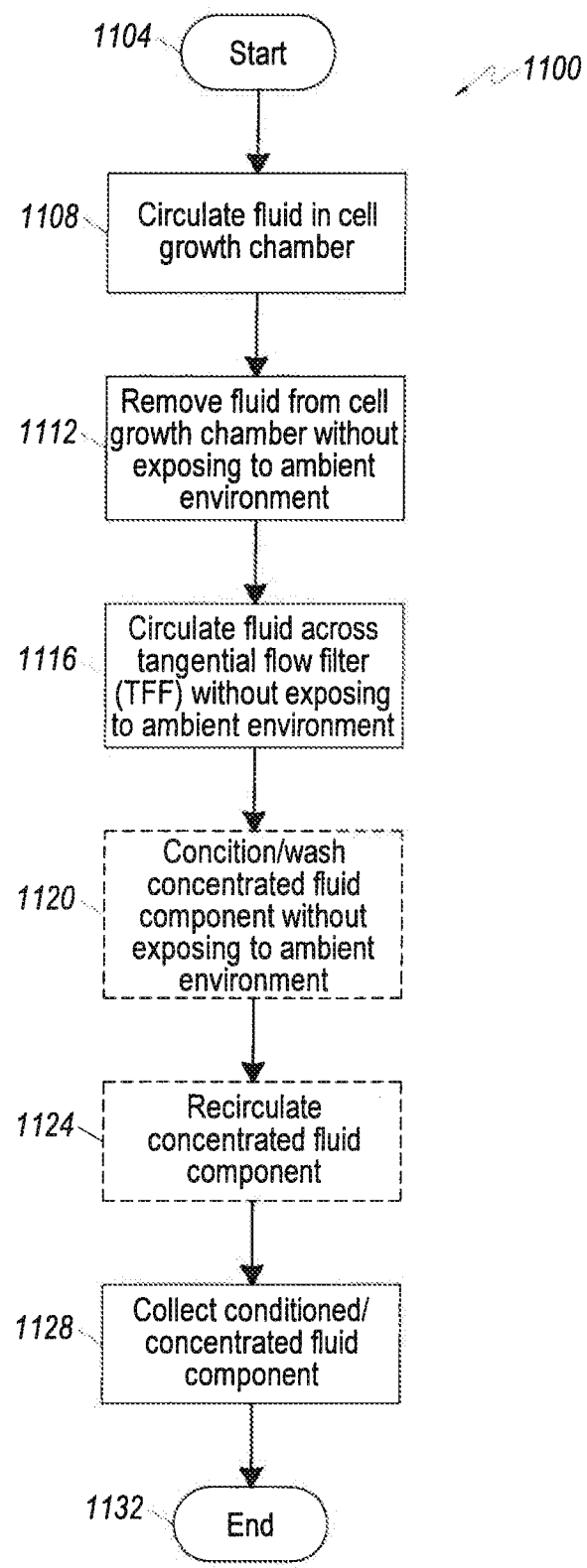
FIG. 11 illustrates a flow diagram depicting the operational characteristics of a process for collecting a concentrated component from a fluid circulated through a cell growth chamber in accordance with embodiments of the present disclosure.

Referring to FIG. 11, flow 1100 beings with START operation 1104, and proceeds to step 1108 where fluid is circulated in a cell growth chamber. Step 1108 may be performed by a CES such as CES 100, 500, or 600. In embodiments, this may involve pumps, valves, or other flow control devices, examples of which are described above. The fluid circulated through the cell growth chamber may contain a number of components. In some embodiments, the fluid may contain cells, media for growing cells, proteins, cellular products (e.g., cytokines, growth factors), buffers, etc.

Next, at step 1112, fluid is removed from cell growth chamber without exposing to ambient environment. Step 1112 may involve use of pumps, valves, or other fluid flow control devices that are part of a closed CES (e.g., CES 100, 500, and 600) to direct fluid out of a cell growth chamber which may be part of the closed CES. At step 1116, the fluid removed from the cell growth chamber at step 1112 is circulated across a TFF, again without exposing it to the ambient environment. Step 1116 may also be performed by pumps, valves and other components of a closed CES such as CES 100, 500, and 600, which directs flow of a fluid exiting a cell growth chamber to a TFF.

The result of step 1116 is two concentrated fluid components. In one embodiment, in which the fluid includes cellular products, such as cytokines or growth factors, one of the two fluid components generated in step 1116 may be concentrated in the cellular products, while the other fluid may be concentrated in other components.

Step 1120 is an optional step that involves conditioning one of the concentrated fluid components and may be performed without exposing the concentrated fluid component to the ambient environment. In some embodiments, step 1120 may be performed during step 1116 when fluid is being circulated across the TFF. In other embodiments, step 1120 may occur after step 1116. In yet other embodiments, step 1120 may involve a number of steps that may occur both during and after step 1116.

In embodiments, the conditioning of step 1120 may involve adding material for a variety of purposes. For example, material may be added to a concentrated fluid component as a cryoprotectant as a step before the concentrated fluid component is frozen. In other embodiments, the material added at step 1120 may deactivate a component that could affect the usefulness of the fluid, such as adding a protein to deactivate tripsin or other release biomolecule. In another embodiment, the material may condition the concentrated component for use in a therapeutic or research process, such as by addition of a preservative.

In another embodiment, conditioning step 1120 may involve a washing step. In these embodiments, the material added at step 1120 is a material that removes or dilutes a component. As one example, a solvent may be added during step 1120, which may occur at the same time as step 1116. The solvent may dissolve a component and carry the component solute across a membrane of the TFF into a fluid. In other embodiments, the solvent may not dissolve the component but still carry the component across a membrane of the TFF.

At optional step 1124, a concentrated fluid from step 1116 is recirculated back to the TFF without exposing the concentrated fluid to the ambient environment. Step 1124 may be performed in order to further concentrate components of the fluid, and may be performed using pumps, valves, and other fluid flow control devices that may be part of a CES.

In one embodiment, step 1124 may be performed as part of washing step at step 1120. In this embodiment, steps 1116, 1120, and 1124 are repeated, namely a wash material (e.g., solvent or diluent) is added at 1120, the concentrated fluid with the wash material is recirculated back to the TFF at 1124, and step 1116 is performed to remove at least some of the wash material, which may contain a component being removed from the concentrated fluid. This is merely one example and step 1124 may be performed independent of any washing step.

In other embodiments, step 1124 involves recirculating a concentrated fluid component back to the bioreactor. In some embodiments, if the fluid includes cells that are generating cellular products, and flow 1100 is being performed to collect the cellular products, step 1124 may be performed in order to return any cells in the concentrated fluid back to the cell growth chamber in order to allow to generate additional cellular components.

At step 1128, the concentrated fluid component, which may have been optionally washed or conditioned, is collected. The collection occurs without exposure to the ambient environment. Flow 1100 ends at 1132.

Figure 12:
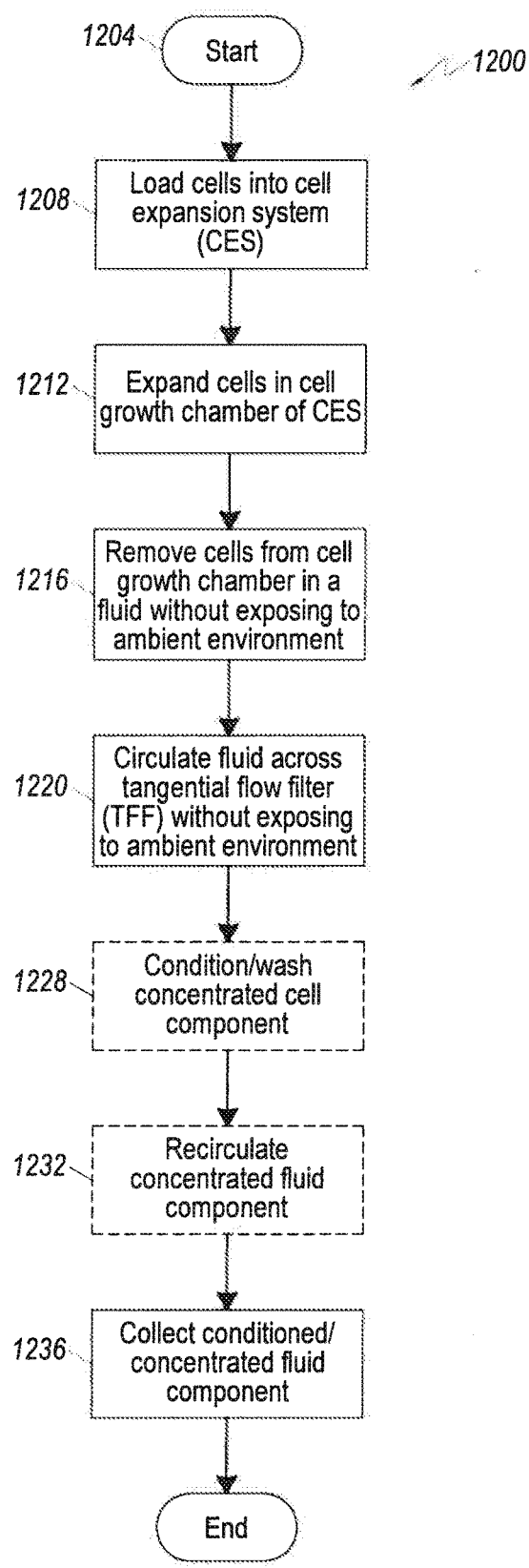
FIG. 12 illustrates a flow diagram depicting the operational characteristics of a process for collecting expanded cells from a fluid circulated through a cell growth chamber in accordance with embodiments of the present disclosure.

Referring to FIG. 12, flow diagram 1200 illustrates a process of expanding/growing cells and concentrating the cells within a closed system, in accordance with an embodiment of the present invention. Flow 1200 begins with START operation 1204, and proceeds to step 1208 where cells are loaded into a cell expansion system. The cells may be loaded in a fluid carrying the cells into a cell growth chamber. As described above with respect to CES 100, 500, and 600, the CES may have a number of components including fluid flow components such as valves, pumps, sensors, air removal chambers, gas transfer modules etc. Step 1208 may involve operation of one or more of these components of the CES.

From 1208, flow 1200 passes to step 1212 where cells are expanded in a cell growth chamber that is part of the CES. Step 1212 may also involve operation of a number of components of the CES. For example, different fluids may be circulated throughout the CES, including a cell growth chamber. The fluid may contain nutrients for promoting the growth of the cells.

After step 1212, flow passes to step 1216 where the cells are removed from the cell growth chamber without exposing to ambient environment. In embodiments, the cells are removed in a fluid that is circulated through the cell growth chamber. Step 1112 may involve use of pumps, valves, or other fluid flow control devices that are part of a closed CES (e.g., CES 100, 500, and 600) to direct fluid out of a cell growth chamber which may be part of the closed CES. In some embodiments, the removal of the cells from the cell growth chamber may involve use of a releasing agent to release cells that may adhere to the growth chamber. As those with skill in the art may appreciate, some cell types are adherent and grow while they are adhered to a surface, such as hollow fibers in a cell growth chamber. Step 1216 may therefore involve a number of steps prior to removing the cells out of the cell growth chamber in a fluid.

At step 1220, the fluid removed from the cell growth chamber that includes the cells, is circulated across a TFF, again without exposing it to the ambient environment. Step 1220 may also be performed by pumps, valves and other components of a closed CES such as CES 100, 500, and 600, which directs flow of a fluid exiting a cell growth chamber to a TFF.

The result of step 1220 is two concentrated fluid components. A first concentrated cell component, includes cells removed from the cell growth chamber at step 1216. A second concentrated fluid component includes other components.

Step 1228 is an optional step that involves conditioning one of the concentrated fluid component or concentrated cell components and may be performed without exposing the fluid component to the ambient environment. In some embodiments, step 1228 may be performed during step 1220 when fluid is being circulated across the TFF. In other embodiments, step 1228 may occur after step 1220. In yet other embodiments, step 1228 may involve a number of steps that may occur both during and after step 1220.

In embodiments, the conditioning of step 1228 may involve adding material for a variety of purposes. For example, material may be added to the concentrated cell component as a cryoprotectant as a step before the concentrated cell component is frozen. In other embodiments, the material added at step 1120 may deactivate a component that could affect the usefulness of cells in the concentrated cell component, such as adding a protein to deactivate tripsin, which is used in some embodiments as a cell releasing agent. In another embodiment, the material may condition the concentrated cell component for use in a therapeutic or research process, such as by addition of a preservative.

In another embodiment, conditioning step 1228 may involve a washing step. In these embodiments, the material added at step 1228 is a material that removes or dilutes a component. As one example, a solvent may be added during step 1228, which may occur at the same time as step 1220. The solvent may dissolve a component and carry the component solute across a membrane of the TFF into a fluid and out of what will be the concentrated cell component. In other embodiments, the solvent may not dissolve the component but still carry the component across a membrane of the TFF.

At optional step 1232, the concentrated cell component generated at step 1220 is recirculated back to the TFF without exposing the concentrated cell component to the ambient environment. Step 1124 may be performed in order to further concentrate cells in the concentrated cell component, and may be performed using pumps, valves, and other fluid flow control devices that may be part of a CES.

In one embodiment, step 1232 may be performed as part of washing step at step 1228. In this embodiment, steps 1220, 1228, and 1232 are repeated, namely a wash material (e.g., solvent or diluent) is added at 1228, the concentrated fluid with the wash material is recirculated back to the TFF at 1232, and step 1220 is performed to remove at least some of the wash material, which may contain a component being removed from the concentrated fluid. This is merely one example and step 1232 may be performed independent of any washing step.

At step 1236, the concentrated fluid component, which may have been optionally washed or conditioned, is collected. The collection occurs without exposure to the ambient environment.

Figure 13:
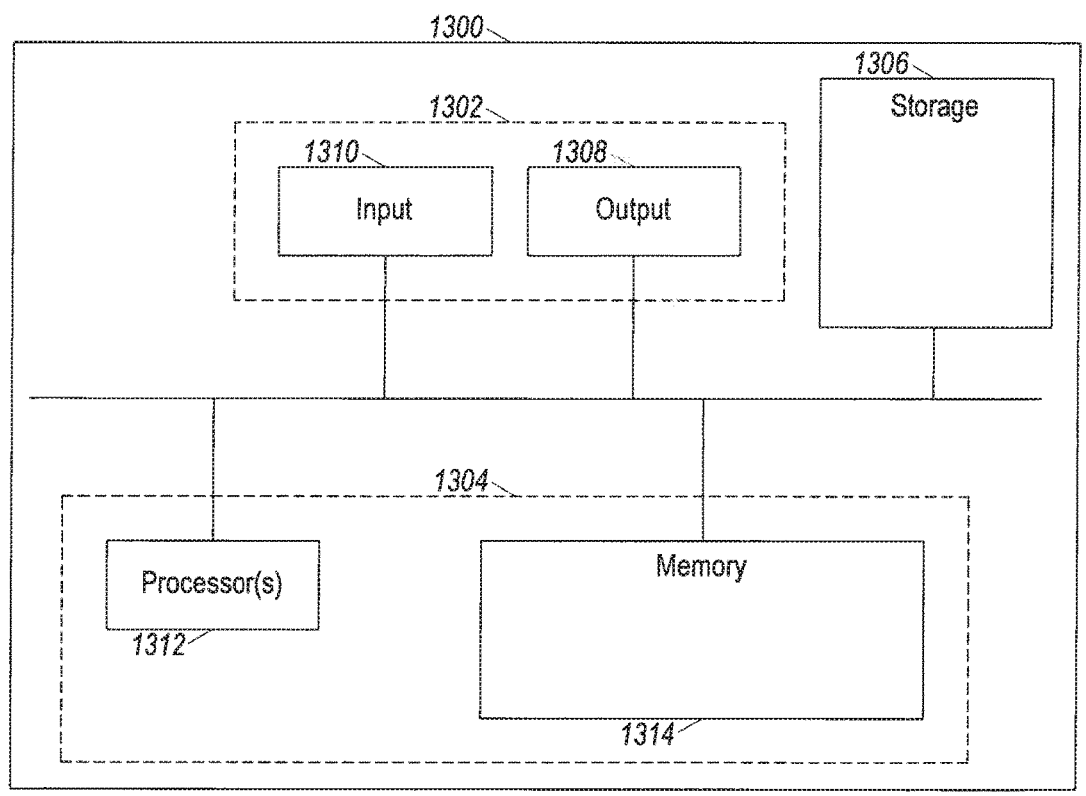
FIG. 13 depicts a processing system upon which embodiments of the present disclosure may be implemented.

Finally, FIG. 13 illustrates example components of a computing system 1300 upon which embodiments of the present disclosure may be implemented. Computing system 1300 may be used in embodiments, for example, where a cell expansion system uses a processor to execute tasks, such as custom tasks or pre-programmed tasks performed as part of processes such as processes 1100 and 1200 described above. For example, a pre-programmed task may include, "Concentrate and Remove Cellular Product" or "Concentrate and Remove Cells".

The computing system 1300 may include a user interface 1302, a processing system 1304, and/or storage 1306. The user interface 1302 may include output device(s) 1308, and/or input device(s) 1310 as understood by a person of skill in the art. Output device(s) 1308 may include one or more touch screens, in which the touch screen may comprise a display area for providing one or more application windows. The touch screen may also be an input device 1310 that can receive and/or capture physical touch events from a user or operator, for example. The touch screen may comprise a liquid crystal display (LCD) having a capacitance structure that allows the processing system 1304 to deduce the location(s) of touch event(s), as understood by those of skill in the art. The processing system 1304 may then map the location of touch events to UI elements rendered in predetermined locations of an application window. The touch screen may also receive touch events through one or more other electronic structures, according to embodiments. Other output devices 1308 may include a printer, speaker, etc. Other input devices 1310 may include a keyboard, other touch input devices, mouse, voice input device, etc., as understood by a person of skill in the art.

Processing system 1304 may include a processing unit 1312 and/or a memory 1314, according to embodiments of the present disclosure. The processing unit 1312 may be a general purpose processor operable to execute instructions stored in memory 1314. Processing unit 1312 may include a single processor or multiple processors, according to embodiments. Further, in embodiments, each processor may be a multi-core processor having one or more cores to read and execute separate instructions. The processors may include general purpose processors, application specific integrated circuits (ASICs), field programmable gate arrays (FPGAs), other integrated circuits, etc., as understood by a person of skill in the art.

The memory 1314 may include any short-term or long-term storage for data and/or processor executable instructions, according to embodiments. The memory 1314 may include, for example, Random Access Memory (RAM), Read-Only Memory (ROM), or Electrically Erasable Programmable Read-Only Memory (EEPROM), as understood by a person of skill in the art. Other storage media may include, for example, CD-ROM, tape, digital versatile disks (DVD) or other optical storage, tape, magnetic disk storage, magnetic tape, other magnetic storage devices, etc., as understood by a person of skill in the art.

Storage 1306 may be any long-term data storage device or component. Storage 1306 may include one or more of the systems described in conjunction with the memory 1314, according to embodiments. The storage 1306 may be permanent or removable. In embodiments, storage 1306 stores data generated or provided by the processing system 1304.

It will be apparent to those skilled in the art that various modifications can be made to the apparatus, systems, and methods described herein. Thus, it should be understood that the embodiments are not limited to the subject matter discussed in the Specification. Rather, the present disclosure is intended to cover modifications, variations, and/or equivalents. The acts, features, structures, and/or media are disclosed as illustrative embodiments for implementation of the claims.

Various components may be referred to herein as "operably associated." As used herein, "operably associated" refers to components that are linked together in operable fashion, and encompasses embodiments in which components are linked directly, as well as embodiments in which additional components are placed between the two linked components.

The foregoing discussion of the one or more present inventions has been presented for purposes of illustration and description. The foregoing is not intended to limit the one or more present inventions to the form or forms disclosed herein. This disclosure is not to be interpreted as reflecting an intention that the claimed invention requires more features than are expressly recited in each claim. Rather, as the following claims reflect, inventive aspects lie in less than all features of a single foregoing disclosed embodiment. Thus, the following claims are hereby incorporated into this Detailed Description, with each claim standing on its own as a separate embodiment of the one or more present inventions.

Moreover, though the description of the one or more present inventions has included description of one or more embodiments and certain variations and modifications, other variations and modifications are within the scope of the invention (e.g., as may be within the skill and knowledge of those in the art, after understanding the present disclosure). It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

It will be apparent to those skilled in the art that various modifications and variations can be made to the methods and structure of the present invention without departing from its scope. Thus it should be understood that the invention is not be limited to the specific examples given. Rather, the invention is intended to cover modifications and variations within the scope of the following claims and their equivalents.

What is claimed is:

1. A method of concentrating a cellular component from a fluid circulated in a cell growth chamber, the method comprising:
    expanding cells within a cell growth chamber, wherein the cell growth chamber comprises a hollow fiber membrane with an intracapillary space and an extracapillary space, wherein the expanding further comprises:
        circulating, with a first pump, fluid in the intracapillary space of the cell growth chamber, the fluid comprising nutrients that promote cell growth;
        expanding the cells in the intracapillary space;
        circulating, with a second pump, media within the extracapillary space and through an oxygenator to provide oxygen to the cells;
    removing expanded cells from the cell growth chamber using the fluid;
    circulating, with the first pump, the fluid with the expanded cells across a tangential flow filter that is fluidly associated with the cell growth chamber, as part of a closed system, to generate a concentrated fluid component and a concentrated cell component, wherein the fluid flows out of a port of the cell growth chamber and directly into the tangential flow filter without exposure to the ambient environment;
    recirculating, with the first pump, the concentrated cell component across the tangential flow filter to further concentrate the cells in the concentrated cell component;
    collecting at least a portion of the concentrated fluid component in a container; and
    collecting at least a portion of the further concentrated cellular component in a container.

2. The method of claim 1, further comprising:
    before circulating the fluid across the tangential flow filter, adding a second fluid to the fluid.

3. The method of claim 1, further comprising:
    before recirculating the concentrated cell component across the tangential flow filter, adding a second fluid to the concentrated cell component.

4. The method of claim 1, wherein the recirculating is performed until a predetermined concentration of cells in the concentrated cell component is reached.

5. The method of claim 1 further comprising:
    introducing the concentrated cell component back into the cell growth chamber.

* * * * *